(12) United States Patent
Dilernia et al.

(10) Patent No.: US 10,937,523 B2
(45) Date of Patent: Mar. 2, 2021

(54) METHODS, SYSTEMS AND COMPUTER READABLE STORAGE MEDIA FOR GENERATING ACCURATE NUCLEOTIDE SEQUENCES

(71) Applicant: Emory University, Atlanta, GA (US)

(72) Inventors: Dario A. Dilernia, Atlanta, GA (US); Jung-Ting Chien, Atlanta, GA (US); Eric Hunter, Atlanta, GA (US)

(73) Assignee: Emory University, Atlanta, GA (US)

( * ) Notice: Subject to any disclaimer, the term of this patent is extended or adjusted under 35 U.S.C. 154(b) by 637 days.

(21) Appl. No.: 15/506,949

(22) PCT Filed: Aug. 27, 2015

(86) PCT No.: PCT/US2015/047147
§ 371 (c)(1),
(2) Date: Feb. 27, 2017

(87) PCT Pub. No.: WO2016/033305
PCT Pub. Date: Mar. 3, 2016

(65) Prior Publication Data
US 2018/0121600 A1    May 3, 2018

Related U.S. Application Data

(60) Provisional application No. 62/042,566, filed on Aug. 27, 2014.

(51) Int. Cl.
G16B 30/00    (2019.01)
G16B 45/00    (2019.01)
G16B 30/10    (2019.01)
C12Q 1/6869    (2018.01)

(52) U.S. Cl.
CPC ............ *G16B 30/00* (2019.02); *C12Q 1/6869* (2013.01); *G16B 30/10* (2019.02); *G16B 45/00* (2019.02)

(58) Field of Classification Search
None
See application file for complete search history.

(56) References Cited

PUBLICATIONS

Batzoglou The many faces of sequence alignment Briefings in Bioinformatics vol. 6, pp. 6-22 (Year: 2005).*
Margulies et al. Approaches to comparative sequence analysis: towards a functional view of vertebrate genomes Nature Reviews Genetics vol. 9, pp. 303-313 (Year: 2008).*

* cited by examiner

*Primary Examiner* — John S Brusca
(74) *Attorney, Agent, or Firm* — Meunier Carlin & Curfman LLC

(57) ABSTRACT

Methods, systems and computer-readable storage media relate to generating one or more consensus sequences. The methods may include determining a group of one or more reads with each main position without diversity from a group of one or more aligned reads based on diversity status of each main position, each group including sequence data disposed at a plurality of main positions and a plurality of secondary position regions disposed adjacent to the main positions. The methods may also include determining legitimate sequence data from each second position region having one or more nucleotides for each group of one or more reads without diversity; and generating a consensus sequence including sequence data disposed at each main position without diversity and legitimate sequence data disposed at each secondary position region for each group of one or more reads with each main position without diversity.

20 Claims, 10 Drawing Sheets

Specification includes a Sequence Listing.

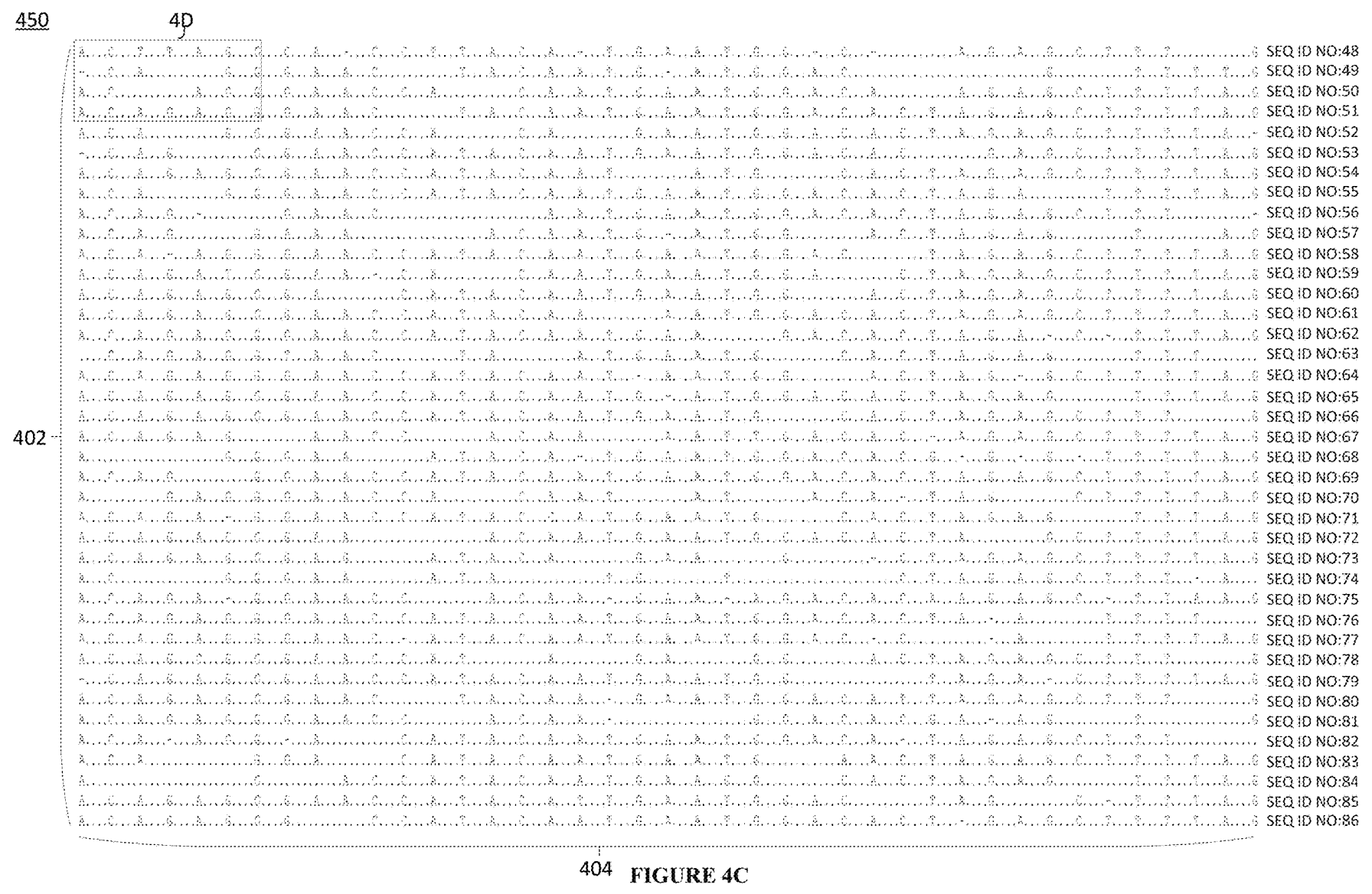

METHODS, SYSTEMS AND COMPUTER READABLE STORAGE MEDIA FOR GENERATING ACCURATE NUCLEOTIDE SEQUENCES

CROSS-REFERENCE TO RELATED APPLICATIONS

This application is the National Stage of International Application No. PCT/US2015/047147 filed Aug. 27, 2015, which claims priority to U.S. Provisional Application No. 62/042,566 filed Aug. 27, 2014. The entirety of each of these applications is hereby incorporated by reference for all purposes.

ACKNOWLEDGEMENTS

This invention was made with government support under Grant No. AI064060 awarded by the National Institutes of Health. The government has certain rights in the invention.

INCORPORATION-BY-REFERENCE OF MATERIAL SUBMITTED VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 14080US_ST25.txt. The text file is 16 KB, was created on Dec. 22, 2017, and is being submitted electronically via EFS-Web.

BACKGROUND

Next-Generation Sequencing (NGS) generally involves a number of new technologies that allow parallel sequencing of several DNA molecules by following in real time the nucleotidic synthesis of the complementary DNA strand to the one that is sequenced as the polymerase mediates the sequencing reaction. The main advantage of these technologies is that they can speed up the sequencing procedure and provide a high number of copies for each sequenced segment. However, many of these techniques are limited to generating a relatively short length of the sequencing products (e.g., reads) and can encounter problems, such as accurately assembling the different nucleotidic variants, when sequencing homologous nucleotidic sequences.

There are systems, such as PacBio Sequencing System, that can generate long reads. However, these systems generally generate long reads with a high error rate and thereby cannot accurately sequence homologous sequences (e.g., moderate or highly homologous nucleotidic sequences).

SUMMARY

Thus, there is a need for a system configured to generate consensus sequence, for example, from homologous nucleotidic sequences.

The disclosure relates to systems, methods, and computer-readable media storing instructions generating one or more consensus sequences.

In some embodiments, the methods relate to a method of processing sequence data to generate one or more consensus sequences from sequence data. The method may include determining a group of one or more reads with each main position without diversity from a group of one or more aligned reads based on diversity status of each main position of the group of one or more aligned reads. Each group may include sequence data disposed at a plurality of main positions and a plurality of secondary position regions disposed adjacent to the main positions. The diversity status may be based on a frequency of one or more nucleotides and/or diversity confidence score of one or more non-consensus nucleotides disposed at each main position in each group. The method may include determining legitimate sequence data from each second position region having one or more nucleotides for each group of one or more reads without diversity. The method may further include generating a consensus sequence including sequence data disposed at each main position without diversity and legitimate sequence data disposed at each secondary position region for each group of one or more reads with each main position without diversity. The methods may be performed by a computer having a memory and a processor.

In some embodiments, a method may include receiving or obtaining one or more groups of aligned sequence data. The aligned sequence data may include one or more aligned reads of sequence data, each read including sequence data disposed at a plurality of main positions and a plurality of secondary position regions including a plurality of secondary positions disposed adjacent to each main position. In some embodiments, the method may include correcting the sequence data disposed at one or main positions in each read based on the sequence data disposed at the adjacent secondary position region. The method may further include determining a group of one or more reads with each main position without diversity based on a diversity confidence score for each group of the corrected aligned sequence data. The diversity confidence score may be based on a frequency of each nucleotide disposed at each main position in the group. In some embodiments, the method may also include determining legitimate sequence data based on each secondary position region of the group of one or more reads with each main position without diversity in which one or more nucleotides are disposed. The method may further include generating a consensus sequence incorporating sequence data disposed at main positions without diversity and the legitimate sequence data without diversity.

In some embodiments, the methods may further include determining a group of one or more reads with each main position with diversity based on the diversity status of each main position of the group of one or more aligned reads; and classifying the group of one or more reads with each main position with diversity into a fixed number of groups based on a similarity score. In some embodiments, the similarity score may represent a proportional relationship between each pair of reads of the group of one or more reads with each main position with diversity based on a number of differences between each main position with diversity of the pair. In some embodiments, the threshold for the similarity score may be variable and the fixed number of groups may be two. In some embodiments, the similarity score may be based on a corrected distance value.

In some embodiments, the methods may include aligning the sequence data to generate a group of one or more aligned reads. The methods may further include correcting the group of one or more aligned reads. The correcting may include correcting the sequence data disposed in one or more main positions and the adjacent secondary position region based on one or more nucleotides being disposed in the adjacent secondary position region.

In some embodiments, the disclosure may relate to a system for processing sequence data to generate one or more consensus sequences from sequence data. The system may include a processor and a memory. The system may be configured to cause determining a group of one or more reads with each main position without diversity from a group of one or more aligned reads based on diversity status of each main position of the group of one or more aligned reads. Each group may include sequence data disposed at a plurality of main positions and a plurality of secondary position regions disposed adjacent to the main positions. The diversity status may be based on a frequency of one or more nucleotides and/or diversity confidence score of one or more non-consensus nucleotides disposed at each main position in each group. The system may be further configured to cause determining legitimate sequence data from each secondary position region having one or more nucleotides of the group of one or more reads without diversity. The system may be further configured to cause generating a consensus sequence including sequence data disposed at each main position without diversity and legitimate sequence data disposed at each secondary position region for each group of one or more reads with each main position without diversity.

In some embodiments, the disclosure may relate to a computer-readable medium storing instructions for processing sequence data to generate one or more consensus sequences from sequence data. The medium may be a non-transitory medium. In some embodiments, the instructions may include determining a group of one or more reads with each main position without diversity from a group of one or more aligned reads based on diversity status of each main position of the group of one or more aligned reads. Each group may include sequence data disposed at a plurality of main positions and a plurality of secondary position regions disposed adjacent to the main positions. The diversity status may be based on a frequency of one or more nucleotides and/or diversity confidence score of one or more non-consensus nucleotides disposed at each main position in each group. The instructions may further include determining legitimate sequence data from each secondary position region having one or more nucleotides of the group of one or more reads without diversity. The instructions may also include generating a consensus sequence including sequence data disposed at each main position without diversity and legitimate sequence data disposed at each secondary position region for each group of one or more reads with each main position without diversity.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIG. 4A shows an example of aligned sequence data according to embodiments;

FIG. 4C shows an example of corrected aligned sequence data according to embodiments;

DESCRIPTION OF THE EMBODIMENTS

Figure 1:
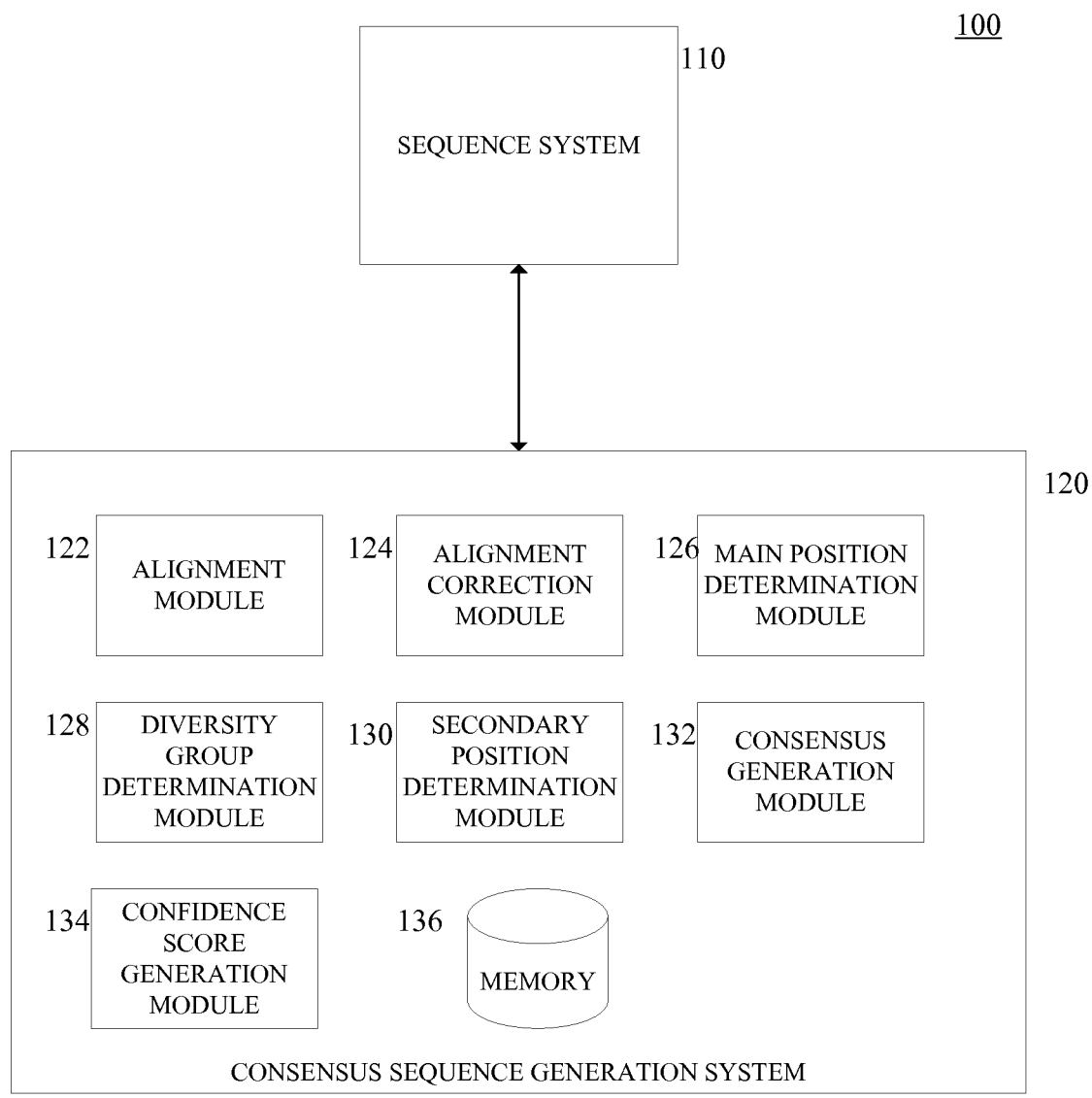
FIG. 1 shows a block diagram illustrating a system according to embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosed methods, systems, and computer-readable media relate to a system capable of generating one or more consensus sequences. The disclosure can generate highly accurate one or more consequence consensus sequences from nucleotide sequence data obtained from a next generation sequencing system. The disclosure can differentiate sequencing reads that belong to different but yet closely related genomes. In this way, the disclosure can generate highly accurate consensus sequence for each of the multiple DNA molecules present in a mixture sequenced in one single sequence run. Also, the disclosure can analyze the outputs obtained during one single sequencing run performed either on non-homologous as well as on highly homologous DNA molecules.

A "biomolecule" may refer to any molecule that is produced by a biological organism, including large polymeric molecules such as proteins, polysaccharides, lipids, and nucleic acids (DNA and RNA) as well as small molecules such as primary metabolites, secondary metabolites, and other natural products.

DNA (deoxyribonucleic acid) is a chain of nucleotides consisting of 4 types of nucleotides: A (adenine), T (thymine), C (cytosine), and G (guanine); and that RNA (ribonucleic acid) is comprised of 4 types of nucleotides: A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand.

As used herein, "nucleotide sequence data," "nucleotide sequence information," "genetic sequence," "sequence data," "sequence information or "sequence read" can denote any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA, RNA, cDNA, and/or other genetic sequencing data. The sequence data can obtained using all available varieties of techniques, platforms or technologies including, but not limited to next generations sequencing systems (e.g., Ion Personal Genome Machine® (PGM™) System for Next-Generation Sequencing, SOLiD® Sequencing System of Life, etc.), among others, or a combination thereof. Some examples of next generation sequencing techniques can include, but are not limited to, sequencing by synthesis, sequencing by ligation, and sequencing by hybridization.

A "nucleotide" can refer to the base themselves, to nucleosides, or to nucleotides comprising the bases. For example, the letters (also referred to as "nucleotide identifiers" and/or nucleotide types), "A" denotes deoxyadenosine, "C" denotes deoxycytidine, "G" denotes deoxyguanosine, and "T" denotes thymidine.

FIG. 1 shows an example of a system 100 capable of generating one or more consensus sequences from sequence data. The system 100 may include any number of modules and/or systems that communicate with other through electrical or data connections (not shown). In some embodiments, the modules and/or systems may be connected via a wired or data network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

In some embodiments, any of the modules and/or systems of the system 100 may be at least in part be based on cloud computing architecture. In some embodiments, the modules and/or systems may be applied to a self-hosted private cloud based architecture, a dedicated public cloud, a partner-hosted private cloud, as well as any cloud based computing architecture.

Although the modules of the system are shown as being directly connected, the modules may be indirectly connected to one or more of the other modules of the system. In some embodiments, a module may be only directly connected to one or more of the other modules of the system.

It is also to be understood that the system may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

As shown in FIG. 1, the system 100 may include a sequence system 110 configured to obtain sequence data, for example, by performing a sequencing run in which a number of molecules are subjected to nucleotide sequence procedures. The sequence system 110 may be any sequencing platform or technology including, but not limited to next generations sequencing systems (e.g., Ion Personal Genome Machine® (PGM™) System for Next-Generation Sequencing, SOLID® Sequencing System of Life, etc.).

In some embodiments, the system 100 may include a consensus sequence generation system 120 configured to generate one or more consensus sequences from the sequence data. In some embodiments, the consensus sequence generation system 120 may obtain or receive the sequence data directly from the sequence system 110, indirectly from the sequence system 110 (e.g., through a database), among others.

In some embodiments, the consensus sequence generation system 120 may include an alignment module 122 configured to align the sequence data using an assembly system (such as Pacific Biosciences Quiver) for example, into a matrix having a plurality of reads. In some embodiments, the aligned sequence data may include a plurality of reads. Each read can correspond to a DNA sequence. The reads can be any length. The reads may be long, short, or any combination. For example, the length of the read can average about 8,000 letters (e.g., ACCACTGTA) but can be more or less. In some embodiments, one or more reads may also be longer than 20,000 letters and may be as short as about 50 letters. In some embodiments, the aligned sequence data may correspond to a plurality of reads arranged in a matrix, in the aligned sequence data, each read may correspond to one line of information (e.g., a sequence).

Figure 4A:
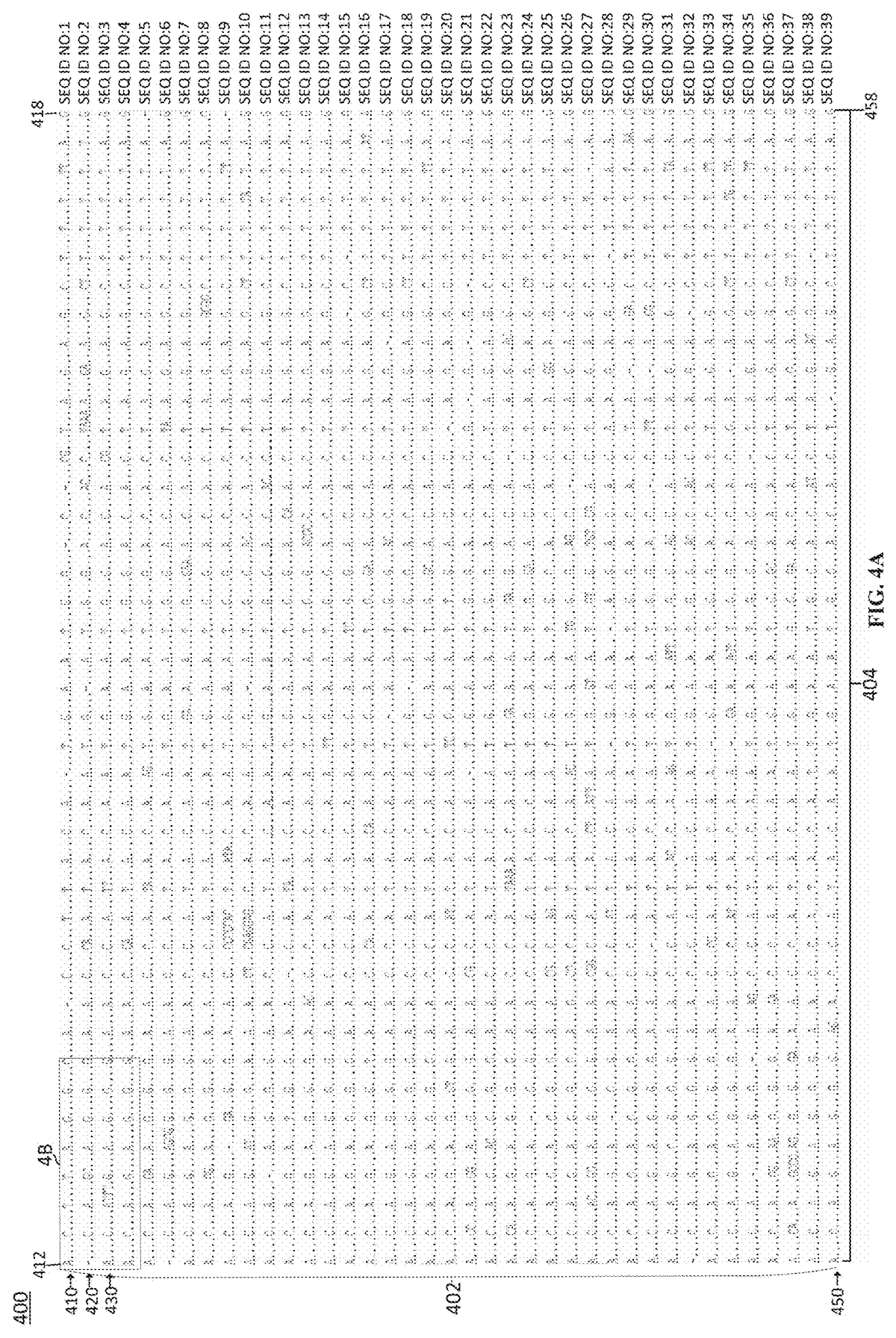
Figure 4B:
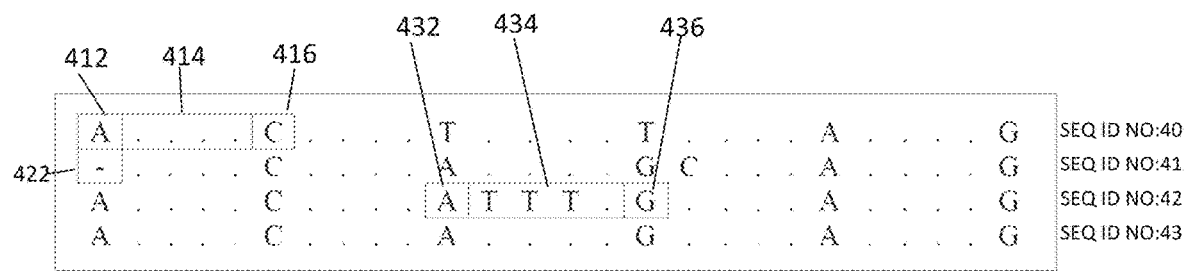
FIG. 4B shows an enlarged view of a portion of the example shown in FIG. 4A.
Figure 4D:
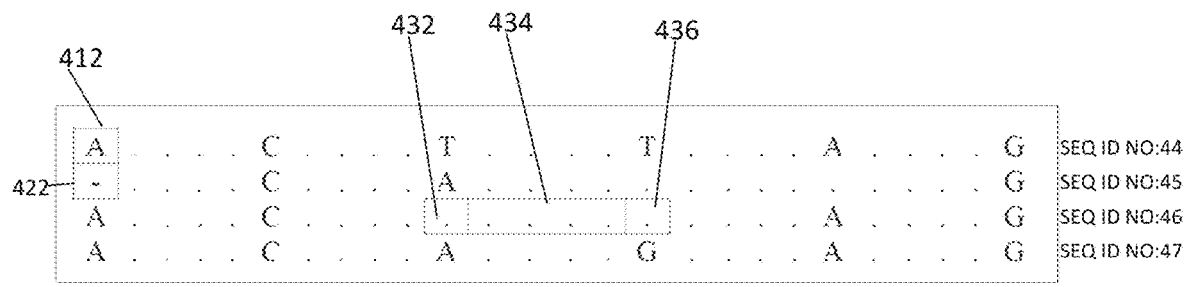
FIG. 4D shows an enlarged view of a portion of the example shown in FIG. 4C.

FIGS. 4A and B show an example of sequence information 400 generated from an alignment module 122 according to embodiments. As shown in FIGS. 4A and B, the aligned sequence data 400 may include a plurality of reads 402 (e.g., reads 410, 420, 430, . . . 450). Each read may correspond to a row in the matrix. The aligned sequence data 400 may also include sequence data disposed at a plurality of positions 404 (e.g., positions 412 . . . 418). Each position may correspond to a column in the matrix. In some embodiments, an identifier representing specific sequence data or information may be disposed at each position. The identifier may include a nucleotide identifier (also referred to as nucleotide) representing a nucleotide (e.g., A, C, G, or T) or a blank identifier representing no information. In some embodiments, the blank identifier may be a symbol representing no information and/or a symbol representing machine-error (e.g., deletion). In some embodiments, the blank identifier may include more than one identifier. For example, the blank identifier may include a symbol representing a blank (no information)(e.g., (.)) and a symbol representing a possible error or deletion (-). An insertion can be a single nucleotide or multiple nucleotides (e.g., A, C, G, or T) that can be misincorporated between two "real" or "legitimate" nucleotides during the sequencing process. A deletion can be a "hole" in a read generated by the sequencing machine, for example, by accidentally skipping one of the nucleotides during the sequencing process.

In some embodiments, each read of the aligned sequence data may include sequence data disposed at a plurality of main positions and a plurality of secondary position regions of one or more secondary positions. A main position may be considered a position with a high probability of including a legitimate nucleotide. A secondary position region may be considered one or more positions with a high probability of including an error or technique-driven insertions. A secondary position region may be disposed adjacent to one or more main positions. For example, each secondary position region may be disposed after and/or before each main position. In each read, each main position may correspond to the position in the first column (i) and every position in the nth column proceeding the first position. For example, the main position may correspond to the position in the first column (i) and positions(s) in every fifth column (i+5) after the first column. By way of example, as shown in FIGS. 4A and B, in read 410, positions 412 and 416 correspond to main positions. The positions 412 and 416 correspond to columns 1 and 6, respectively. In each read, each secondary position region may correspond to a fixed number of positions adjacent to a main position (e.g., before and/or after a main position). In some embodiments, the secondary position region may include any number of positions corresponding to one or more secondary positions. For example, the secondary position region may include any number between and including 1-5 secondary positions. In some embodiments, the secondary position region may include more than 5 secondary positions. By way of example, as shown in FIGS. 4A and B, the second position region may include four positions (e.g., columns) disposed before, after, and/or between each main position. In the example, each secondary position region in FIGS. 4A and B includes four (secondary) positions. For example, secondary position region 414 disposed between the main positions 412 and 416 includes four secondary positions that respectively correspond to columns 2-5. An identifier (symbol (.)) is disposed at each position in the secondary position region 414.

In some embodiments, the aligned sequence data (e.g., aligned sequence data 400) may be stored in a memory 136. In some embodiments, the aligned sequence data may be stored so that the sequence data is associated with the coordinate information (row and column) of the aligned sequence data. For example, the sequence data may be identified by a read identification and a position identification. By way of example, with respect to FIGS. 4A and B, the nucleotide "A" may be associated with an identification for the first read 410 and with an identification for the first position 412 in the memory 136. In some embodiments, for the data disposed in the secondary position regions, the sequence data may be disposed with respect to the specific secondary position and read, the specific secondary position region and read, or a combination thereof. For example, with respect to FIGS. 4A and B, the blank identifiers " . . . " may be associated with each secondary position of the secondary position region 414 and the first read 410, respectively, in the memory 136 and may be associated with the secondary position region 414 and the first read 410 in the memory 136.

In some embodiments, the system 120 may include an alignment correction module 124 configured to correct the aligned sequence data. The alignment correction module 124 may be configured to correct the sequence data disposed at one or more main positions and adjacent secondary position region based on one or more nucleotides disposed in the secondary position region. The alignment correction module 124 may be configured to correct the sequence data disposed at one or more main positions by (i) removing a nucleotide identifier disposed in a main position based on a nucleotide identifier being disposed in an adjacent secondary position region; (ii) removing each nucleotide identifier disposed in each secondary position within the adjacent secondary position region; or (iii) a combination thereof. In some embodiments, like the aligned sequence data, the corrected aligned sequence data may be stored in the memory 136 so that the corrected sequence data is associated with the coordinate information (e.g., position identification and read identification).

For example, as shown in FIGS. 4A and B, the nucleotide identifier "T" is disposed in the three secondary positions in a secondary position region (434) between main positions 432 and 436 in which nucleotide identifiers (A and G, respectively) are disposed. The correcting step 306 may remove the nucleotide identifiers disposed in those main positions (432 and 436) and the nucleotide identifier(s) disposed in each position of the secondary position region (434), as shown in FIGS. 4C and D. In this way, errors (e.g., method or machine-driven insertions and/or deletions ("IN-DELs") generated by the sequencing machine can be minimized. Also, although a portion (e.g., up to about 15%) of the original sequence information can be removed by the alignment correction module 124, the corrected aligned sequence data includes data (e.g., nucleotides) that are less likely to be technique-driven errors thereby providing a more robust input for processing by the system 120 to generate a consensus sequence.

In some embodiments, the system 120 may include a main position determination module 126 configured to determine a diversity status of each main position of the corrected aligned sequence data. Diversity status may include "with diversity," and "without diversity." A main position "with diversity" represents a main position with evidence of a mixture of nucleotides (e.g., evidence of diversity). A main position "without diversity" represents a main position with evidence of a single "legitimate" or "real" nucleotide. A main position "without diversity" may correspond to a main position determined to include only a consensus nucleotide or non-consensus nucleotide(s) with diversity confidence score(s) outside of the threshold requirements.

In some embodiments, the diversity status may be based on a diversity confidence score and/or frequency. In some embodiments, the diversity confidence score for each main position may be based on non-consensus nucleotide(s) (the nucleotide(s) other than the dominant or consensus nucleotide).

In some embodiments, a main position "with diversity" may correspond to a main position with one or more non-consensus nucleotides having a diversity confidence score that satisfies one or more threshold requirements. The diversity confidence score for a main position that satisfies one or more threshold requirements may represent evidence of a mixture of legitimate nucleotides (e.g., nucleotide diversity) disposed at that position. In some embodiments, the diversity confidence score may be based on a frequency of one or more non-consensus nucleotides disposed at a main position. The diversity confidence score for a main position that does not satisfy one or more threshold requirements may represent evidence of a single (e.g., non-mixture) legitimate nucleotide disposed at that position. For example, a diversity confidence score for a non-consensus nucleotide disposed at a main position that is outside of the threshold requirements can represent an error or background noise. In this way, one or more main position(s) with diversity may be differentiated from one or more positions with background noise. Thus, by discarding positions that are likely to provide nothing more than background noise, the system 120 can focus on processing the positions exhibiting the most informative data.

In some embodiments, the main position determination module 126 may determine whether the group of one or more reads includes one or more main positions with diversity based on the diversity status of each main position.

In some embodiments, if one or more main positions of the group is with diversity, the main position determination module 126 may generate a group of one or more reads with only the main position(s) with diversity (also referred to as a group of one or more reads with one or more main positions with diversity). The main positions without diversity may be excluded from the group of one or more reads with diversity. In this way, the main position determination module 126 can generate a group of one or more reads with only the one or more main positions that has evidence of a mixture of legitimate nucleotides (e.g., nucleotide diversity).

In some embodiments, if the main position determination module 126 determines that each main position of the group is without diversity, the main position determination module 126 may determine that the group is a group of one or more reads with each main position without diversity. In this way, the main position determination module 126 can identify a group of one or more reads that has evidence of legitimate sequence data being disposed at each main position.

In some embodiments, the system 120 may include a group determination module 128 configured to classify each group of reads with each main position with diversity into a number of groups (e.g., subgroups) of one or more reads, for example, based on a similarity score. The similarity score may correspond to a measure of similarity between each pair of two reads of the group based on the main position(s) with diversity. The similarity score may correspond to a quantifiable measurement representing a proportional relationship between each pair of reads based on the differences between the main position(s) with diversity of a number of reads. In some embodiments, a similarity score may be determined for each relationship of reads (e.g., a similarity score for read 1 and read 2, read 1 and read 3, etc.). In some embodiments, the number of differences may be based on a frequency of nucleotide types. A higher similarity score can represent a higher number of differences between reads. In some embodiments, the number of groups may be fixed and the one or more threshold requirements for the similarity score may be variable. The number of groups may be predefined and may correspond to any number (e.g., two, three, four, etc.). In some embodiments, the group determination module 128 may be configured to classify each group of one or more reads with each main position with diversity into two groups of one or more reads.

In this way, a specific threshold, which can be impossible to determine in most datasets, for the similarity score may not be necessary to classify the reads into groups. Additionally, predefining the number of groups can allow for a better and more accurate exploration of the sequence data. For example, reads that differ by one single nucleotide can be accurately reconstructed.

In some embodiments, each group of reads determined by the group determination module 128 may be stored in the memory 136. In some embodiments, for each group of one or more reads determined by the group determination module 128, the alignment module 122 can be configured to reconstruct the read(s) to include the sequence data stored in the memory 136 and align the sequence data for the read(s) of each group and the alignment correction module 124 can be configured to align and correct the aligned sequence data for each group.

In some embodiments, the system 100 may include a secondary position determination module 130 configured to determine whether legitimate sequence data is disposed at each secondary position and/or secondary position region based on a diversity confidence score for each group of one or more reads with each main position without diversity. The diversity confidence score may be based on a frequency of each nucleotide disposed in the each secondary position region and/or each secondary position. In some embodiments, the diversity confidence score may provide evidence to distinguish between a secondary position and/or secondary position region with a "legitimate" nucleotide and a secondary position and/or secondary position region with a nucleotide from noise or error. The secondary position determination module 130 may be configured to determine a legitimate nucleotide (e.g., an identifier) disposed at one or secondary position regions when the diversity confidence score for that nucleotide at that region meets one or more threshold requirements. In this way, a large number of errors generated by the alignment module 122 and related to the level of signal obtained for each nucleotide type during the sequencing process can be resolved, thereby the system 120 can generate more accurate consensus sequences.

In some embodiments, the system 120 may include a consensus generation module 132 configured to generate a consensus sequence to include the sequence data disposed at one or more main positions of the group of one or more reads with each main position without diversity determined by the main position diversity determination module 126 and the sequence data (e.g., legitimate nucleotides) disposed at one or more secondary position regions determined by the secondary position determination module 130 for each group of one or more reads with each main position without diversity. The consensus generation module 132 may generate a number of consensus sequences. The number of consensus sequences may correspond to the number of groups of reads with each main position without diversity In some embodiments, the system 120 may include a confidence score generation module 134 configured to determine one or more confidence parameters for the consensus sequence. The one or more confidence parameters may include any number of confidence parameters. In some embodiments, the one or more confidence parameters may include a first confidence parameter, a second confidence parameter, among others, or a combination thereof. In this way, the one or more confidence parameters can summarize the main characteristics of each final alignment and indicate the accuracy of the consensus sequence without the need of reanalyzing the entire dataset.

In some embodiments, the system 120 may include the memory 136 configured to temporarily and/or permanently store the output from each of the modules 122-134. In some embodiments, the memory may be any data storage device configured to store data. Examples of the memory include hard drives, network attached storage (NAS), read-only memory, random-access-memory, CD-ROMS, CD-Rs, CD-RWS, magnetic tapes, other storage devices, or a combination thereof.

Figure 2:
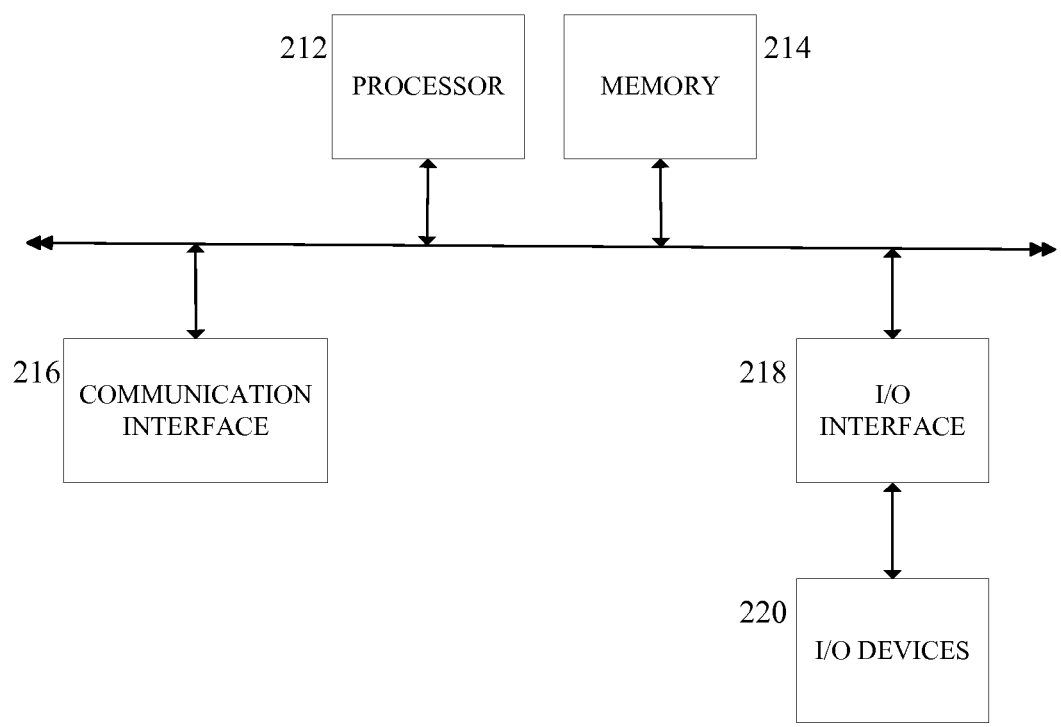
FIG. 2 shows a block diagram illustrating an example of a computing system.

One or more of the modules and/or systems of system 100 may be and/or include a computer system and/or device. FIG. 2 is a block diagram showing a computer system 200. The modules of the computer system 200 may be included in at least some of the systems and/or modules, as well as other devices of system 100.

The systems may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radiofrequency network, or another similarly functioning wireless network.

It is also to be understood that the systems may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the systems may be time synchronized. In further embodiments, the systems may be time synchronized with other systems, such as those systems that may be on the medical facility network.

The system 200 may be a computing system, such as a workstation, computer, or the like. The system 200 may include one or more processors 212. The processor(s) 212 (also referred to as central processing units, or CPUs) may be any known central processing unit, a processor, or a microprocessor. The CPU 212 may be coupled directly or indirectly to one or more computer-readable storage media (e.g., memory) 214. The memory 214 may include random access memory (RAM), read only memory (ROM), disk drive, tape drive, etc., or a combinations thereof. The memory 214 may be configured to store programs and data, including data structures. In some embodiments, the memory 214 may also include a frame buffer for storing data arrays.

In some embodiments, another computer system may assume the data analysis or other functions of the CPU 212. In response to commands received from an input device, the programs or data stored in the memory 214 may be archived in long term storage or may be further processed by the processor and presented on a display.

In some embodiments, the system 210 may include a communication interface 216 configured to conduct receiving and transmitting of data between other modules on the system and/or network. The communication interface 216 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 210 may include an input/output interface 218 configured for receiving information from one or more input devices 220 (e.g., a keyboard, a mouse, and the like) and/or conveying information to one or more output devices 220 (e.g., a printer, a CD writer, a DVD writer, portable flash memory, etc.). In some embodiments, the one or more input devices 220 may configured to control, for example, the generation of the consensus sequence(s), the display of the consensus sequence(s) on a display, the printing of the consensus sequence(s) by a printer interface, among other things.

Figure 3:
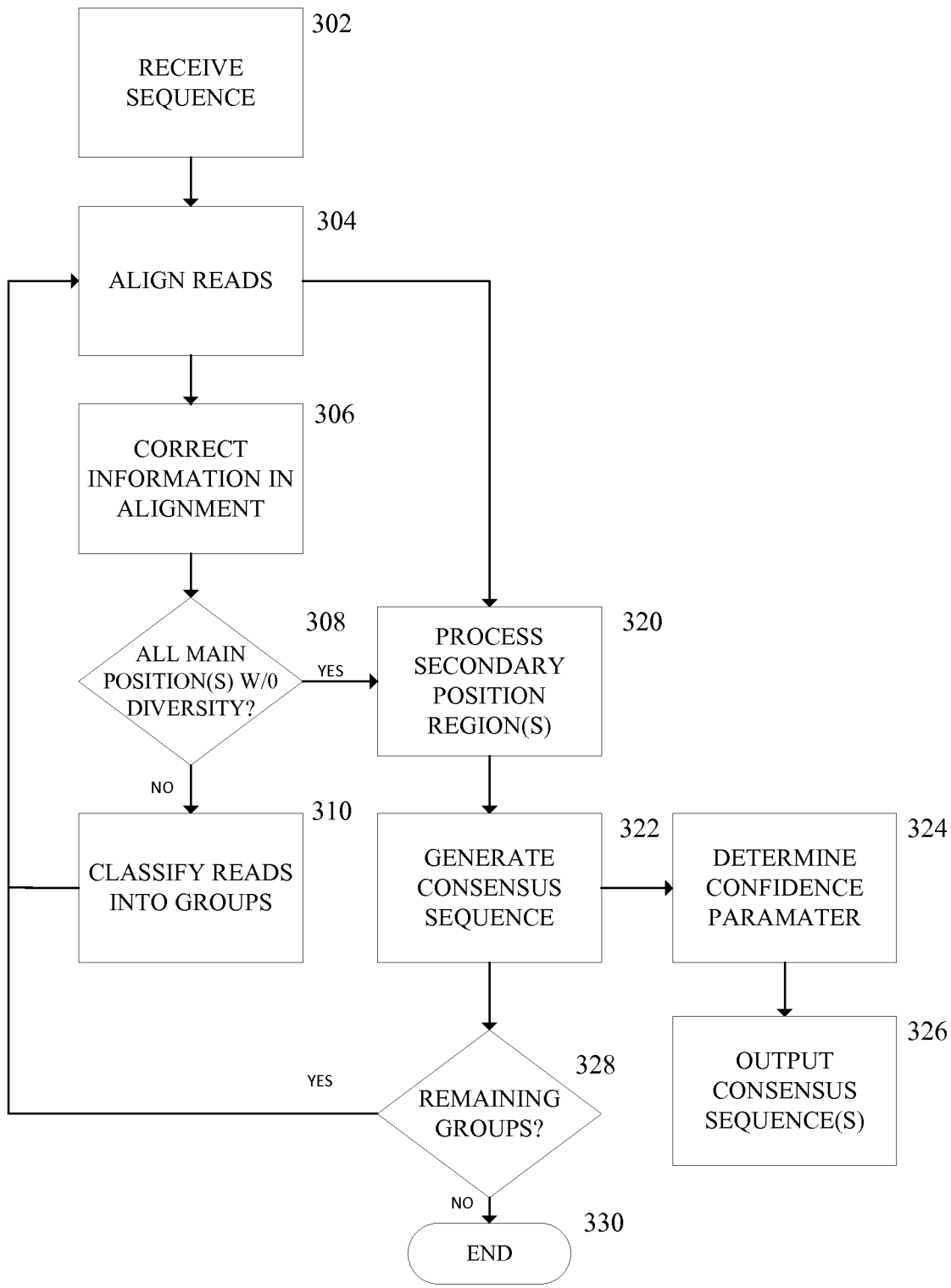
FIG. 3 shows a method of generating a consensus sequence according to embodiments.

FIG. 3 illustrates a method 300 for processing aligned sequence information to generate one or more consensus sequences. The system for carrying out the embodiments of the methods disclosed herein is not limited to the systems shown in FIGS. 1 and 2. Other systems may be used.

The methods of the disclosure are not limited to the steps described herein. The steps may be individually modified or omitted, as well as additional steps may be added. It will be also understood that at least some of the steps may be performed in parallel. For example, any steps 304-326 may be performed in parallel. In this way, one or more groups of sequence data may be processed in parallel.

Unless stated otherwise as apparent from the following discussion, it will be appreciated that terms such as "aligning," "classifying," "grouping," "comparing," "generating," "determining," "obtaining," "processing," "computing," "selecting," "receiving," "correcting," "estimating," "calculating," "quantifying," "outputting," "acquiring," "analyzing," "approximating," "continuing," "resuming," "using," "retrieving," "sorting," "incorporating," "removing," "moving," "proceeding," "performing," "reconstructing," "replacing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

In some embodiments, the methods can identify and correct errors in the sequence information on a read-by-read basis. In some embodiments, the methods can first identify and correct errors in the sequence data disposed at main positions of each read before identifying and correcting errors in the sequence data disposed at the secondary positions of each read. In this way, the sequence data for the main positions can be accurately determined before the sequence data for the secondary positions are determined.

In some embodiments, method 300 may include a step 302 of receiving sequence data, for example, from a sequencing system 120.

In some embodiments, the method may include a step 304 of aligning the sequence data into a matrix, for example, using the alignment module 122. In some embodiments, the sequence data may be aligned by other assembly systems. An example of aligned sequence information is shown in FIG. 4A. The step 304 may also include storing the aligned sequence data, for example, in the memory 136.

In some embodiments, the method 300 may include a step 306 of correcting the aligned sequence data, for example, by the alignment correction module 124. In some embodiments, the correcting may be based on an identifier disposed in a secondary position region. In some embodiments, the correcting step 306 may include removing a nucleotide identifier disposed in a main position based on a nucleotide identifier being disposed in an adjacent secondary position region. In some embodiments, the correcting step 306 may include removing each nucleotide identifier disposed at a main position that is adjacent to a secondary position region in which a nucleotide identifier is disposed. The correcting step 306 may also include removing each nucleotide identifier disposed in each secondary position within the adjacent secondary position region(s). For example, as shown in FIGS. 4A and B, the nucleotide identifier (T) is disposed in the three secondary positions in a secondary region (434) between main positions 432 and 436 in which nucleotide identifiers (A and G, respectively) are disposed. The correcting step 306 can remove the nucleotide identifiers disposed in those main positions (432 and 436) and the nucleotide identifier(s) disposed in each position of the secondary position region (434), as shown in FIGS. 4C and D.

This step can minimize the errors generated by the sequencing machine (e.g., method or machine-driven INDELs). In this way, accuracy can be improved because the impact of these errors can be minimized in the sequence data being analyzed.

Figure 5:
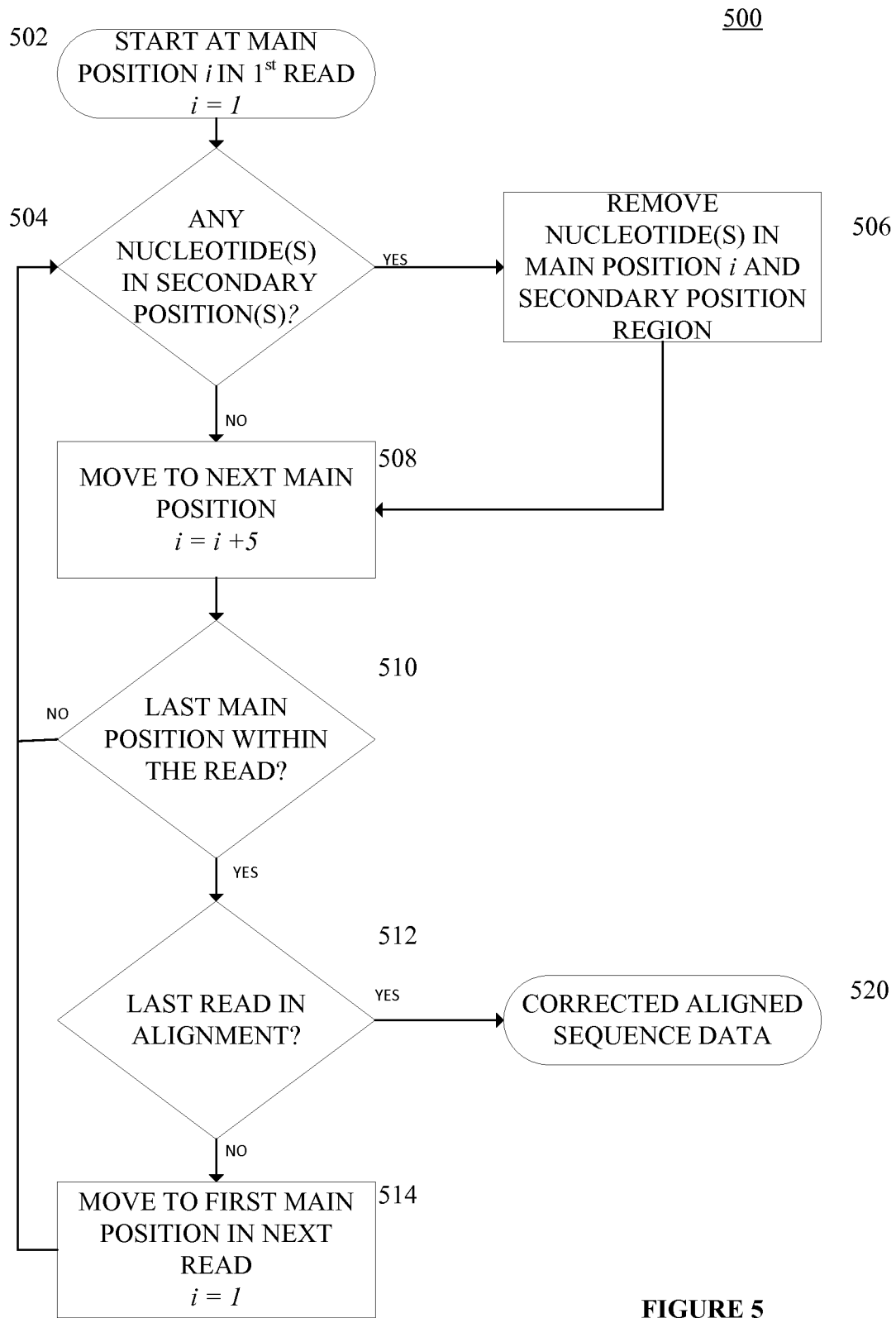
FIG. 5 shows a method of correcting the aligned sequence data according to embodiments.

FIG. 5 shows a method 500 of correcting the aligned sequence data in one or more main positions in each read based on the sequence data disposed in a secondary position region, for example, by the alignment correction module 124. The method 500 may begin at the first position (i) of the first read in the matrix (502). For example, the method 500 can begin at position 412 in read 410 shown in FIGS. 4A and B.

In some embodiments, the method 500 may include a step 504 of determining whether there are any nucleotides in the secondary position region adjacent to the main position (i). If there are no nucleotides in the secondary position region (NO at the step 504), the method 500 may move to the next main position (step 508). For example, with respect to FIG. 4A, the step 504 may determine whether there is a nucleotide disposed in any secondary positions of the secondary position region 414. If there are no nucleotides disposed in the secondary position region 414, the method 500 may then move to the next main position 416 (step 508).

If the step 504 determines that there is one or more nucleotides disposed in the secondary position region adjacent to the main position (YES at step 504), the method 500 may include a step 506 of replacing the nucleotide identifier disposed at the main position(s) adjacent to the secondary position region and at one or more secondary positions in the adjacent secondary position region with a blank identifier. For example, with respect to FIGS. 4A and B, if the step 504 processed the main position 432 in the read 430, the method 500 may proceed to the step 506 of replacing the nucleotide identifiers from the main position 432 ("A") and the main position 436 ("G") and the one or more secondary positions of the secondary position region 434 ("TTT") with a blank identifier (.). FIGS. 4C and D show an example of a matrix corrected according to embodiments. As shown in FIGS. 4C and D, the main positions 432 and 436 and each position of the secondary position region 434 include "." By way of another example, if there are no secondary region positions adjacent to the main position, for example, the main position 418 in the read 410, the method 500 could proceed to step 508 (NO at step 504).

The method 500 may include a step 508 of moving to the next main position. For example, with respect to processing the main position 412 in read 410, in the step 504, the method 500 may move to the main position 416 in the step 508. By way of another example, with respect to processing the main position 432 of the read 430 in the step 504, the method 500 may move to the main position 436.

The method 500 may repeat the steps 504-508 for each main position in the read. In some embodiments, the method 500 may include a step 510 of determining whether the next main position is the last main position within the read. For example, the step 510 can determine whether the next main position exceeds the read length. If the step 510 determines that the main position processed in step 504 is not the last main position in the read ((NO) at step 510), the method may continue processing the main position(s) in that read (the steps 504-508). For example, with respect to FIG. 4A, the method 500 may repeat the steps 504-508 for the read 410 until it reaches main position 418. At main position 418, the method 500 may determine that the next main position (e.g., next column) exceeds the read length (YES at step 510), i.e., the read does not include any sequence information (no identifier) at that position.

In some embodiments, if the method 500 determines that the processed main position is the last position within the read (YES at step 510), the method 500 may include a step 512 of determining whether that main position is disposed in the last read in the aligned data (step 512). For example, with respect to FIG. 4A, for main position 418, the step 512 may determine that there is an additional read in the alignment (NO at step 514). If the step 512 determines there is at least one additional read in the alignment (NO at step 514), the method 500 may include a step 508 of moving to the first main position in the next read. By way of example, in FIG. 4A, after processing main position 418, the step 514 may move to main position 422 disposed in read 420. The steps 504-514 may be repeated until the method determines that the last read in the aligned sequence data was processed (YES at step 512). When the method 500 determines that the last main position is disposed in the last read in the aligned sequence data (YES at step 512), the processing may end and the corrected aligned sequence data can be generated (520). FIGS. 4C and D show an example of a corrected aligned sequence data for the example shown in FIGS. 4A and B according to embodiments. As shown in FIGS. 4C and D, the corrected aligned sequence may include only blank identifiers in the secondary position regions.

In some embodiments, the corrected aligned sequence data 520 may be stored in a memory, for example, the memory 136. In some embodiments, the corrected aligned sequence data 520 may be stored in a memory (e.g., the memory 136) with the aligned sequence data (step 304) in associated manner (e.g., position and read identifications) for later processing.

It will be understood that the steps of method 500 shown FIG. 5 are not limited to the order shown. The steps may be individually modified or omitted, as well as additional steps may be added. It will be also understood that at least some of the steps may be performed in parallel. For example, in some embodiments, one or more reads may be processed in parallel (steps 502-510) and the steps 512 and 514 may be omitted.

In some embodiments, after correcting the aligned sequence data, the method 300 may first determine the sequence data for one or more main positions for a consensus sequence from the corrected aligned sequence data. For example, the method 300 may include a step 308 of determining diversity status of each main position to determine whether the corrected aligned data includes one or more main positions with diversity. The determining of a diversity status (with diversity and/or without diversity) of each main position may be based on a diversity score.

Figure 6:
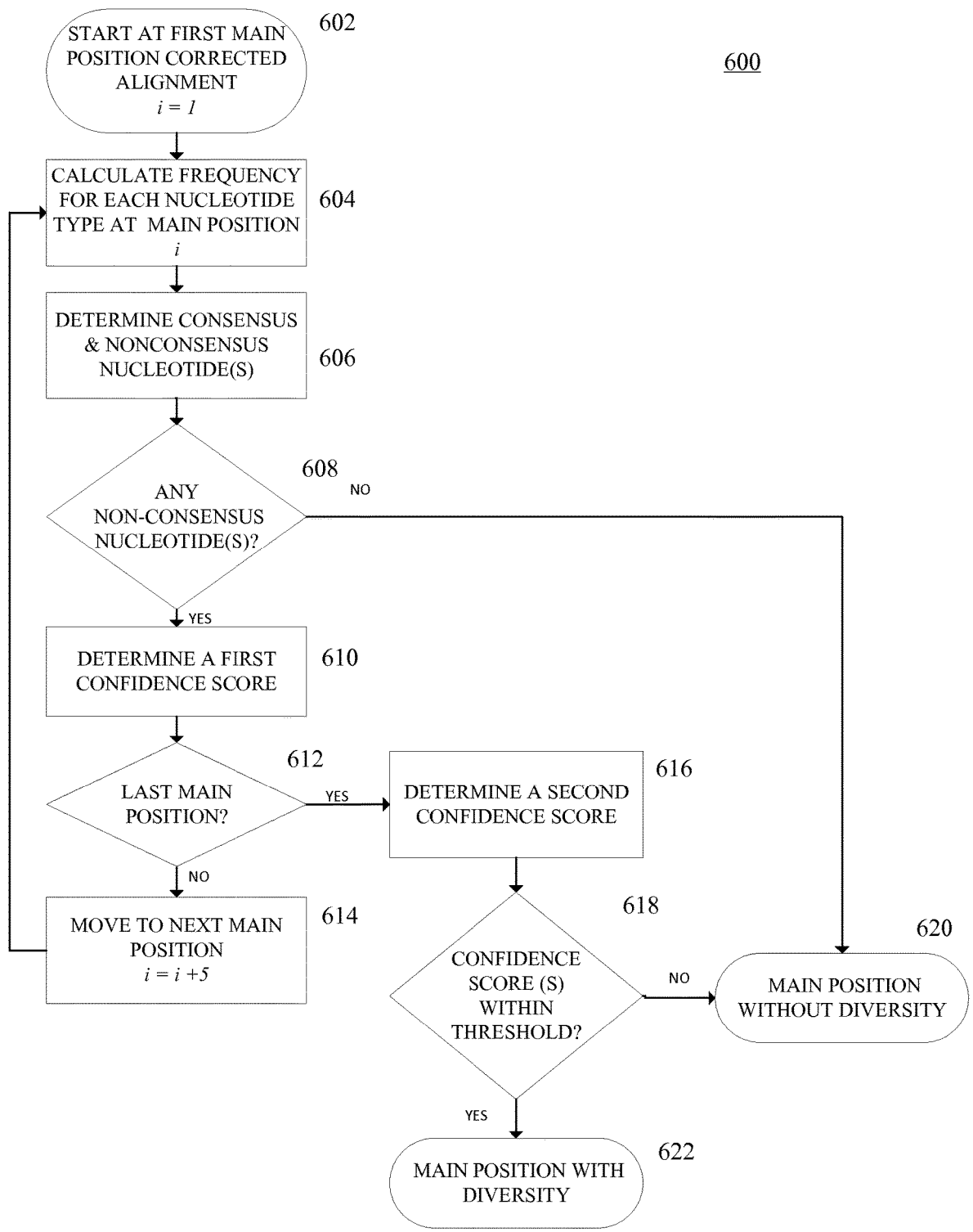
FIG. 6 shows a method of determining a diversity status of each main position of a group of one or more reads according to embodiments.

FIG. 6 shows a method 600 of determining one or more groups of main positions of the corrected aligned sequence based on the diversity status according to embodiments. The diversity status may be based on frequency and/or diversity confidence score. In some embodiments, the diversity status may be determined by other methods.

In some embodiments, the method 600 may start at the first main position i in the corrected aligned sequence data (step 602). FIG. 6 shows steps 602-622 being performed for each main position sequentially, for illustrative purposes only. The steps of FIG. 6 are discussed with respect to a main position i but it will understood that the steps 602-622 of FIG. 6 may be performed for each main position of the corrected aligned sequence data in parallel. By way of example, if the steps are performed for each main position in parallel, then one or more steps of FIG. 6 may be omitted (e.g., steps 612 and/or 614 may be omitted).

In some embodiments, the method 600 may include a step 604 of calculating frequency for each nucleotide (type) disposed at a main position i for all reads in the corrected aligned sequence data (using the nucleotide identifier) (604). The frequency for each nucleotide disposed at the main position i may be stored, for example, in the memory. After determining the frequency of each nucleotide for the main position i (step 604), the method 600 may include a step 606 of determining at least the consensus nucleotide (the dominant nucleotide) for the main position i based on frequency. The consensus nucleotide or dominant nucleotide can correspond to the nucleotide with the highest frequency. The dominant nucleotide can be considered to be a "real" or "legitimate" nucleotide.

The method 600 may include a step 608 of determining whether there are any non-consensus nucleotides disposed at the main position i. The non-consensus nucleotide(s) for the main position i may correspond to the nucleotide(s) other than the consensus nucleotide disposed at the main position i in the corrected aligned sequence data. For example, at the first position 412 in the corrected aligned data 450 in FIGS. 4C and D, "A" is only the nucleotide present in the main position, so there are no non-consensus nucleotides. If there are no non-consensus nucleotides (NO at step 608) (i.e., only a consensus nucleotide), then the main position i may be determined to be a main position without diversity (step 620).

If there are one or more non-consensus nucleotides (YES at step 608), the method 600 may include a step 610 of determining a diversity confidence score for each non-consensus nucleotide for the main position i. The diversity confidence score may be based on frequency. The diversity confidence score may relate to one or more measures of probability of that position having diversity. The diversity confidence score can distinguish between those nucleotide(s) that are likely real or legitimate and those nucleotide(s) that are likely noise or errors (e.g., technique driven errors).

In some embodiments, the diversity confidence score may include more than one diversity confidence score. In some embodiments, the diversity confidence score for each non-consensus nucleotide for each main position may include at least a first diversity confidence score, a second diversity confidence score, among others, or a combination thereof. In some embodiments, the diversity confidence score may include at least a first diversity confidence score and a second diversity confidence score.

In some embodiments, for example, as shown in the FIG. 6, the steps of determining the first and second diversity confidence scores may be performed in separate steps. In some embodiments, the steps of determining the first and second diversity confidence scores may be determined in step 610, for example, if the steps 604-610 are performed for each main position in parallel.

In some embodiment, the first diversity confidence score may relate to a probability of obtaining that nucleotide (e.g., by chance). In this way, the first diversity confidence score may relate to probability that the probability that the nucleotide type is a technique-driven error. In some embodiments, the first diversity confidence score may correspond to a binomial probability value (also known as a "p-value"), for example, determined by a binomial distribution approach. The second diversity confidence score may be based on the first diversity confidence score. In some embodiments, the second diversity confidence score may relate to a corrected first diversity confidence score. In some embodiments, the second diversity confidence score may relate to the probability that a position having diversity is a false positive. In some embodiments, the second diversity confidence score may be q-value determined by a "False discovery rate" (FDR) approach based on the p value. In some embodiments, the diversity confidence score(s) may be different.

In some embodiments, the diversity confidence score may be stored. For example, the first diversity confidence score may be stored in step 610.

In some embodiments, the method 600 may include a step of 612 of determining whether the main position i corresponds to the last main position in the corrected aligned sequence data. If the main position i is not the last main position (NO at step 612), the method 600 may include a step of moving to the next main position (step 614). The method 600 may then repeat the steps 604-612 until the last main position is processed. It will be understood that the steps 612 and/or 614 may be omitted, for example, if each main position is processed in parallel to determine respective diversity confidence score.

In some embodiments, after the method processes each main position (YES at step 612), the method 600 may include a step 616 of determining a second diversity confidence score. As noted above, the second diversity score may alternatively be determined in step 610.

The method 600 may include a step 618 of comparing the diversity confidence score(s) for each non-consensus nucleotide disposed at each main position to one or more threshold requirements to determine whether that main position is a main position with diversity. In some embodiments, the one or more threshold requirements may include a threshold for the first diversity confidence score, the second diversity confidence score, or a combination thereof. In some embodiments, a first diversity confidence score and/or second diversity score higher than the one or more threshold requirements may represent a high probability that a position is a position without diversity. For example, in some embodiments, the threshold requirement may relate to only the second diversity confidence score (e.g., q-value). In some embodiments, the threshold requirement may include additional and/or alternative thresholds for other diversity confidence scores. By way of example, the threshold for the first diversity confidence score may be 0.05 for binomial probability (p-value) and the threshold for the second diversity confidence score may be 0.2 for q-value. For example, the main position(s) with at least one non-consensus nucleotide has a p-value lower than 0.05 and a q-value lower than 0.2 may be considered to be a main position with diversity (622). The main position(s) with each nucleotide type having a p-value higher than 0.05 and a q-value higher than 0.2 (i.e., none of the non-consensus nucleotides disposed at the main position has a p-value lower than 0.5 and a q-value lower than 0.2) may be considered to be a main position without diversity (620) The main position(s) with each non-consensus nucleotide outside the threshold(s) are likely not "real" variations of the sequence (i.e., the non-consensus nucleotide(s) cannot be considered significant). These main position(s) likely differ from the consensus nucleotide due to noise (e.g., an error generated by a machine); and therefore can be grouped with the main position(s) without diversity. In some embodiments, the threshold(s) for the diversity confidence score(s) may be different.

By comparing the diversity confidence score with one or more threshold requirements, the step 618 can separate the main positions into one of two groups: a group of main position(s) with diversity (622) and a group of main position(s) without diversity (620). In some embodiments, the groups 620 and 622 of main positions may be stored, for example, in the memory 136, for later processing.

In some embodiments, based on the determination of the main positions into one of two groups (main position(s) with diversity and main position(s) without diversity), the method 300 may either continue processing the main positions (step 310) or process the secondary positions and/or secondary position regions (step 320). If the step 308 determines that one or more main positions includes diversity (NO at step 308), the method 300 may proceed to classify the reads into a number of sets of a number of groups based on the main positions with diversity.

Figure 7:
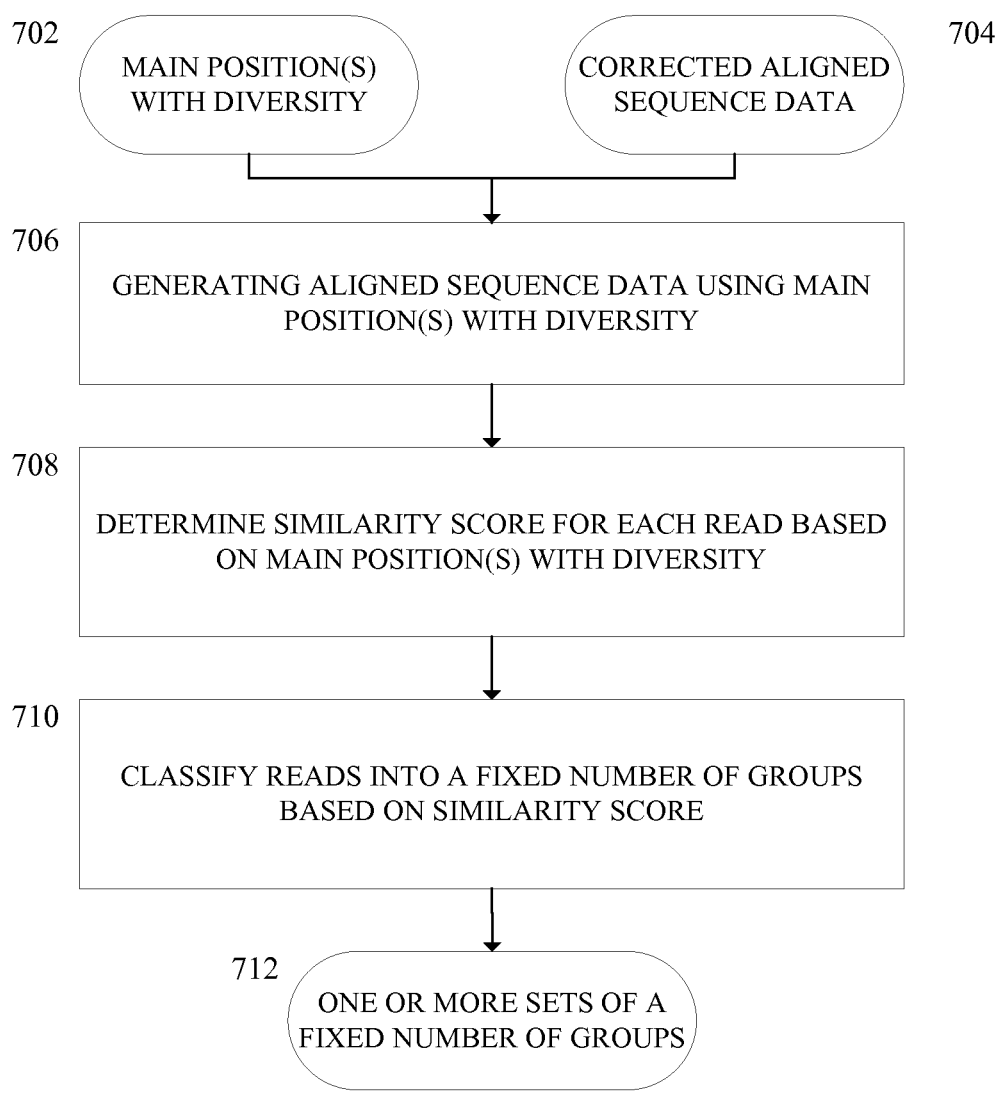
FIG. 7 shows a method of determining a number groups of one or more reads based on main positions with diversity according to embodiments.

FIG. 7 shows a method 700 of processing the main positions with diversity to classify the reads into a number of groups based on similarity scores of the main positions with diversity. By classifying the reads into a number of groups based solely on the main positions with diversity, sensitivity can be improved when distinguishing between reads that belong to the same sequence from reads that belong to different sequence(s), and thus the classification can be more accurate.

As shown in FIG. 7, the method 700 may include a step 706 of generating an aligned sequence data based on the main position(s) with diversity 702 (e.g., output 622 from FIG. 6) and the corrected aligned sequence data 704 (e.g., output 620 from FIG. 6). The aligned sequence data may include all of the reads of the corrected aligned sequence data 704 and each read may only include the identifier(s) from the corrected aligned sequence data 704 disposed at the main position(s) with diversity 702. In this way, the step 706 may generate a matrix of sequence data including the number of rows corresponding to the number of rows in the corrected aligned sequence data 704 and the number of columns corresponding to the number of main position(s) with diversity 702. For example, if the main position(s) with diversity 702 included 18 main positions and the corrected matrix 702 had 423 rows and 9,628 main positions, the aligned sequence data generated in step 706 can include 423 rows and 18 columns.

The method 700 may include a step 708 of determining a similarity score for each relationship of reads provided in the aligned sequence data in the step 706. In some embodiments, the similarity score may be determined so that each read is compared to each remaining read of the group. In this way, the similarity score can be based on a similarity measure between the main position(s) with diversity 702. In some embodiments, the similarity score may be a quantifiable measurement representing a proportional relationship between a pair of reads based on similarity of the main position(s) with diversity 702. In some embodiments, the similarity score may correspond to a weighted distance value. In some embodiments, a high similarity score (e.g., a high distance value) may represent a low similarity between reads. In some embodiments, the distance value may be determined by determining the number of differences between the two reads based on the main position(s) with diversity. In some embodiments, the distance value may be corrected using the frequency of the dominant non-consensus nucleotide for each position, for example, determined in FIG. 6.

By way of example, the distance value may be based on a value representing a probability of diversity for the main position(s) are different in the relationship of the reads. In one embodiment, a diversity value representing a number of different nucleotides (diversity of nucleotides) may be determined for each position of the group based on the frequency of the nucleotides disposed at that position. In one embodiment, the diversity value may be entropy. The higher the diversity value can correspond to higher diversity (e.g., more nucleotide types) at the position type. In some embodiments, other diversity values may be used. In one embodiment, a frequency distribution (or histogram) of the diversity value may be generated to determine a (value representing) probability of diversity for each position. In this example, the distance value for a comparison to two reads corresponds may be based on the values representing probability of diversity for each position for which the reads differ. The distance value for a comparison may correspond to the sum of the values representing probability of diversity for each position for which the reads of a group differ divided by the total number of main positions of the group with diversity.

For example, two reads (read 1 and read 2), of a group having 100 main positions with diversity, differ from each other by three main positions having the following probability of diversity values:

Position 1: 0.64
Position 2: 0.73
Position 3: 0.71

In this example, the corrected distance value for this relationship (e.g. comparison between read 1 and read 2) can be determined as:

$$(1*0.64+1*0.73+1*0.71)/100=0.0208,$$

where 1 represents the unit of distance before correction by the probability of diversity values.

In some embodiments, the similarity score may be determined by other methods.

In some embodiments, the similarity score for each comparison may be stored in a memory, for example, the memory 136, in a similarity score matrix.

In some embodiments, the method 700 may include a step 710 of classifying the reads of the corrected aligned sequence data 704 into a number of groups based on the similarity score. In some embodiments, the classifying may be determined by a clustering analysis.

In some embodiments, the step 710 may classify the reads into a fixed number of groups based on a variable threshold for the similarity score. In some embodiments, the number of groups may be fixed to two. In some embodiments, the fixed number may be a different number (e.g., 1, 3, 4, 5, etc.). In some embodiments, the similarity score threshold may be based on the maximum similarity score determined in the step 708. In this way, the threshold does not need to be pre-defined and can change in every analysis.

In some embodiments, the method 700 may determine one or more sets of a fixed number of groups (720). For example, the method 700 may run in parallel for a number of groups of reads with main positions with diversity. The number of sets can correspond to the number of groups of main positions with diversity determined in FIG. 6 (620).

In some embodiments, after the reads are classified into a fixed number of groups, the method 300 may repeat the steps 304-308 for each group until all main positions of that group are determined to be without diversity. In some embodiments, (sets of) groups may be processed in parallel. In step 304, for each group of one or more reads determined in the step 308, each read may be reconstructed from the sequence data stored in the memory 134 (from the step(s) 302 and/or 304) and the reads in each group may be realigned.

In some embodiments, if the method 300 determines that all main positions of a group of reads are without diversity (YES at the step 308), the group of main positions without diversity can be considered to be legitimate sequence data. In this way, the sequence data disposed at the main positions without diversity of that group may be the basis for a consensus sequence.

After the method determines a group of one more reads with each main position without diversity, the method 300 may include a step 320 of processing each secondary position region of the group to determine whether any secondary position region should be reclassified as a main position (in the consensus sequence). The identifiers disposed in each secondary position region of the group of one more reads to determine whether a legitimate nucleotide is disposed in that region. In some embodiments, the determination of a legitimate nucleotide may be based on a diversity confidence score for each nucleotide that is disposed in the secondary position region.

Figure 8:
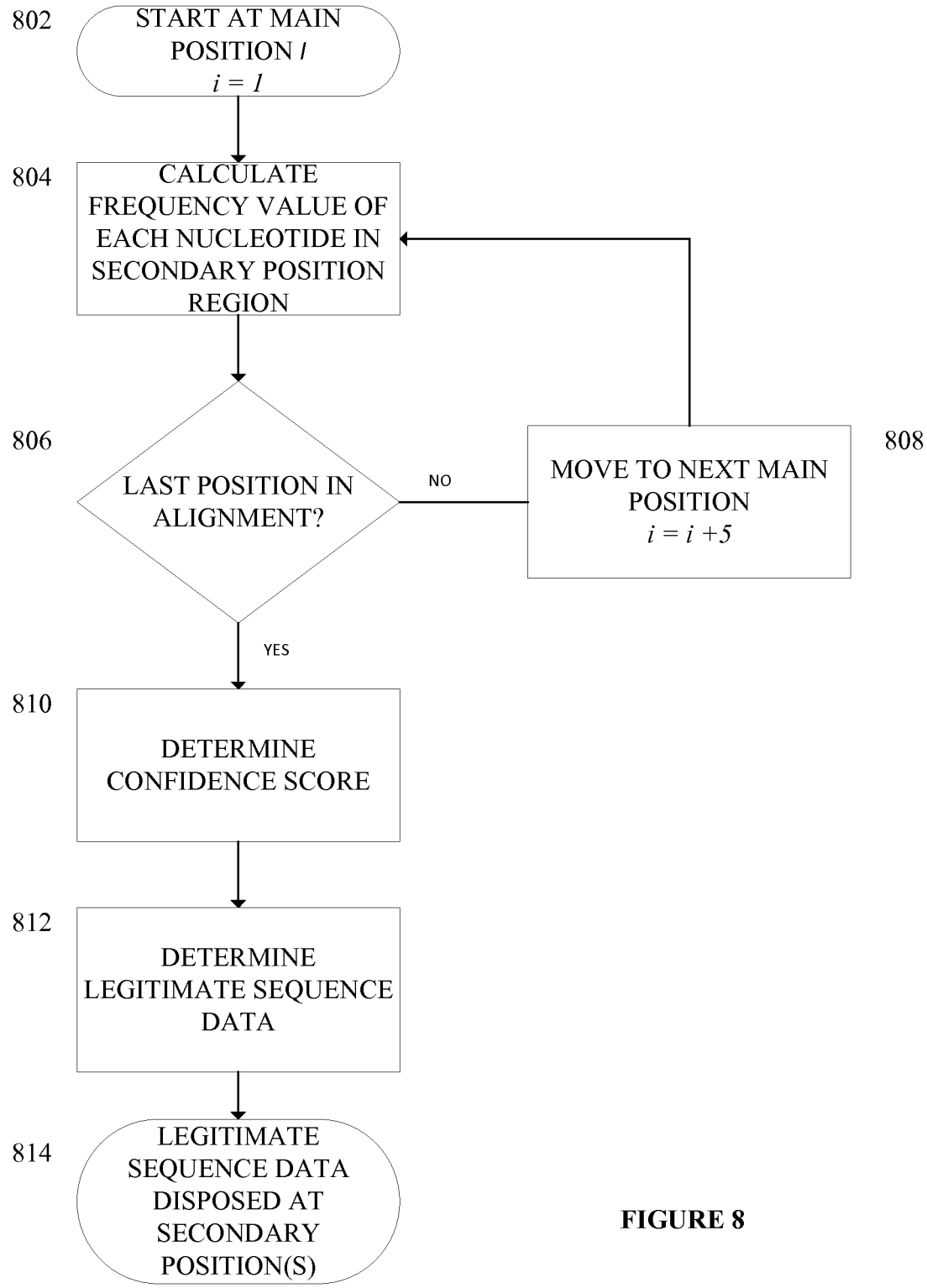
FIG. 8 shows a method of processing secondary position region(s) according to embodiments.

FIG. 8 shows a method 800 of processing the secondary position regions of a group of one or more reads having all main positions without diversity according to embodiments. In some embodiments, other methods may be used.

The method 800 may process the secondary position regions of the aligned sequence data adjacent to each main position. By processing the secondary position regions, each secondary position may be processed to determine whether legitimate sequence data is disposed in the region based on a diversity confidence score. In this way, each secondary position region may be processed to determine whether it was erroneously classified as an error or technique-driven insertions in the aligned sequence data (from the step 304). If the method 800 determines that the secondary position region includes legitimate sequence data, the secondary position region can be reclassified as a main position in the consensus sequence.

In some embodiments, the method 800 can reincorporate the original secondary position regions adjacent to each main position without diversity for each read of the group from the original aligned sequence data (from the step 304), for example, stored in memory 136. In some embodiments, the method 800 may start at the first main position i in the reincorporated aligned sequence data (the step 802).

FIG. 8 shows steps 802-806 being performed for each secondary position region sequentially (based on the main position), for illustrative purposes only. The steps of FIG. 8 are discussed with respect to a main position i but it will understood that steps 802-814 of FIG. 8 may be performed for each main position in parallel. By way of example, if the steps are performed for each main position in parallel, then one or more steps of FIG. 8 may be omitted (e.g., steps 806 and/or 808 may be omitted).

In some embodiments, the method 800 may include a step 804 of calculating frequency for each nucleotide disposed in the secondary position region adjacent to the main position i (using the nucleotide identifier) (604). The frequency for each nucleotide disposed at each secondary position region may be stored, for example, in the memory 134.

In some embodiments, the frequency may be based on a nucleotide type being disposed in the secondary position region for each read. By way of example, one of the reads of the group includes the following sequence data disposed at a secondary position region (i+1, i+2, i+3, i+4):

| Main | i + 1 | i + 2 | i + 3 | i + 4 | Main |
|------|-------|-------|-------|-------|------|
| G | C | C | T | . | C |

In this example, when calculating the frequency of nucleotides for the secondary position region (i+1, i+2, i+3, i+4), "C" may be counted as 1 occurrence although there "C" is disposed at two secondary positions in the secondary position region. In this way, the frequency may not be based on the number of occurrences of a nucleotide disposed in a secondary position region for a read. In some embodiments, the frequency may be determined in a different way.

In some embodiments, the method 800 may include a step of 806 of determining whether the main position i or the secondary position corresponds to the last position in the corrected aligned sequence data. If that position is not the last main position (NO at the step 806), the method 800 may include a step 808 of moving to the next main position. The method 800 may then repeat steps 802-808 until the last position is processed. It will be understood that the steps 806 and/or 808 may be omitted, for example, if each secondary position region is processed in parallel to determine respective diversity confidence score.

In some embodiments, after the frequency for each nucleotide disposed in a secondary position and/or secondary position region is determined, the method 800 may include a step 810 of determining a diversity confidence score for each nucleotide disposed in the secondary position and/or region. The diversity confidence score may be based on frequency. The diversity confidence score can distinguish between those nucleotide(s) that are legitimate and those nucleotide(s) that are noise or errors (e.g., technique driven errors).

In some embodiments, the diversity confidence score may include more than one confidence score. In some embodiments, the diversity confidence score may include at least a first diversity confidence score, a second diversity confidence score, among others, or a combination thereof. In some embodiments, the diversity confidence score may include at least a first confidence score and a second confidence score.

In some embodiments, the first diversity confidence score may relate to a probability of obtaining that nucleotide (e.g., by chance). In this way, the first diversity confidence score may relate to probability that the nucleotide(s) disposed in the secondary position is a technique-driven error nucleotide. In some embodiments, the first diversity confidence score may correspond to a binomial probability value (also known as a "p-value"), for example, determined by a binomial distribution approach. The second diversity confidence score may be based on the first diversity confidence score. In some embodiments, the second diversity confidence score may relate to a corrected first diversity confidence score. In some embodiments, the second diversity confidence score may relate to the probability that a position with a legitimate nucleotide is a false positive. In some embodiments, the second diversity confidence score may be q-value determined by a "False discovery rate" (FDR) approach based on the p value. In some embodiments, the diversity confidence score(s) may be different.

In some embodiments, the method 800 may include a step 812 of determining that a secondary position region includes legitimate sequence data based on the diversity confidence score. In some embodiments, the step 812 can include comparing the diversity confidence score(s) of each secondary position region to one or more threshold requirements to determine whether that secondary position region includes legitimate sequence data. In some embodiments, the one or more threshold requirements may include a threshold for the first diversity confidence score, the second diversity confidence score, or a combination thereof. In some embodiments, a secondary position region with each nucleotide having a first diversity confidence score and/or second diversity confidence score higher than the one or more threshold requirements may represent a secondary position region with a high probability that it does not include legitimate sequence data (i.e., the nucleotide(s) are errors and/or insertions). For example, in some embodiments, the threshold requirement may relate to only the second diversity confidence score (e.g., q-value). In some embodiments, the threshold requirement may include additional and/or alternative thresholds for other diversity confidence scores. By way of example, the threshold for the first diversity confidence score may be 0.05 for binomial probability (p-value) and the threshold for the second diversity confidence score may be 0.2 for q-value. For example, the secondary position regions(s) with at least one nucleotide having p-value lower than 0.05 and a q-value lower than 0.2 may be considered to be a region with legitimate sequence data. The nucleotide type(s) disposed at that secondary position region may be considered to be a legitimate nucleotide type(s) and therefore may be considered to be a main position. The secondary position regions(s) with each nucleotide having a p-value higher than 0.05 and a q-value higher than 0.2 may be considered to a region without legitimate sequence data. The nucleotide type(s) disposed at that secondary position region may be considered to be technique-driven errors and therefore may not be considered to be a main position (e.g., remain as part of the secondary position region). In some embodiments, the threshold(s) for the diversity confidence score(s) may be different.

The method 800 may output the secondary position region(s) and corresponding legitimate sequence data (i.e., sequence data disposed at the secondary position regions having diversity confidence score(s) satisfying the threshold requirements) (814). The secondary position region(s) having legitimate sequence data may be considered to be a main position and incorporated into the consequence sequence accordingly.

By way of example, the secondary position region 414 in FIGS. 4A and B includes nucleotides A, C and G (but not T). In this case, the method 800 can calculate a diversity confidence score for each nucleotide type. For example, if the diversity confidence score for one of the nucleotides (e.g., A) meets the threshold requirement(s), then the method 800 can determine that nucleotide (e.g., "A") is legitimate. The secondary position region 414 can be then be considered to be a main position for the consensus sequence. For example, when the method 300 generates the consensus sequence, the method 300 can insert "A" disposed in region 414 "A" of position 412 and the "C" of position 416.

The method 300 may include a step 322 of generating a consensus sequence including the nucleotide(s) disposed at the main position(s) without diversity determined in the step 308 and at the nucleotide(s) disposed at secondary position region(s) determined in the step 320.

In some embodiments, the method may include a step 324 of determining a one or more confidence parameters for the generated consensus sequence. The method 300 may determine any number of confidence parameters. In some embodiments, the one or more confidence parameters may include a first confidence parameter relating to sequencing coverage. In some embodiments, the first confidence parameter may be based on the number of reads used to generate the consensus sequence. The first confidence parameter may correspond to a value representing the minimum coverage per position. The minimum coverage per position may correspond to a number of reads having the sequence data that include all of the positions provided in the consensus sequence. By way of example, if a DNA consensus sequence has 9854 positions, there can be 9854 values for coverage for that consensus sequence. With respect to this example, if the minimum coverage per position is 24, then all the positions in the consensus sequence were obtained from the information present in at least 24 reads. So, in this example, at least 24 reads were used to determine each of all the positions in the generate consensus sequence.

In some embodiments, the one or more confidence parameters may include a second confidence parameter. The second confidence parameter may relate to the maximum frequency of the non-consensus nucleotide and/or the frequency of the information presented in the consensus sequence. A higher frequency of the non-consensus nucleotides can be associated with a lower confidence in a sequence. In above example, the frequency of the most frequent non-consensus nucleotide can be determined for the DNA consensus sequence having 9854 positions so there can be 9854 values. In this example, if the maximum non-consensus frequency is 0.24, then information presented in the consensus sequence was presented in 76% (1-0.24) of the reads.

In some embodiments, the step 324 may determine other and/or additional confidence parameter(s).

In some embodiments, the method 300 may include a step 326 of outputting the consensus sequence(s). In some embodiments, the outputting may include displaying, printing, storing, and/or transmitting the results. The results may include one or more consensus sequences and/or confidence parameter associated with each consensus sequence.

In some embodiments, the method 300 may include a step 328 of determining whether there are any remaining group(s) and/or set(s) of group(s) of reads with main position(s) with diversity. In some embodiments, the method 300 may repeat the steps 304-328 for each group until all determined groups include main position(s) without diversity. In some embodiments, the groups may be processed in parallel. If all groups have been processed, the method 300 may stop (step 330).

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network or the Internet.

In some embodiments, the disclosed methods (e.g., FIGS. 3, 5 and 6-8) may be implemented using software applications that are stored in a memory and executed by a processor (e.g., CPU) provided on the system 100. In some embodiments, the disclosed methods may be implanted using software applications that are stored in memories and executed by CPUs distributed across the system 100. As such, any of the systems and/or modules of the system 100 may be a general purpose computer system, such as system 200, that becomes a specific purpose computer system when executing the routine of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 2.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method of processing sequence data to generate one or more consensus sequences from sequence data, comprising:
determining a group of reads with a main position without diversity from a group of aligned reads based on diversity status of each main position of the group of aligned reads, the group of aligned reads including sequence data disposed at a plurality of main positions and four or more secondary position regions disposed adjacent to each of the main positions, the diversity status being based on a frequency of one or more nucleotides and/or a diversity confidence score of one or more non-consensus nucleotides disposed at each main position in each group, wherein each main position comprises one or more nucleotides, and further wherein a main position without diversity comprises a main position determined to include only a consensus nucleotide or non-consensus nucleotides with diversity confidence scores outside of a threshold requirement, wherein the plurality of main positions comprises at least 100 main positions and further wherein the group of reads comprises at least 39 reads;
determining legitimate sequence data from each secondary position region having one or more nucleotides for each group of one or more reads without diversity; and
generating a consensus sequence including sequence data disposed at each main position without diversity and legitimate sequence data disposed at each secondary position region for each group of reads with the main position without diversity.

2. The method according to claim 1, further comprising:
determining a group of reads with each main position with diversity based on the diversity status of each main position of the group of aligned reads; and
classifying the reads of the group of reads with each main position with diversity into a fixed number of groups based on a similarity score.

3. The method according to claim 2, wherein the similarity score represents a proportional relationship between each pair of reads of the group of reads with each main position with diversity based on a number of differences between each main position of the pair.

4. The method according to claim 2, wherein a threshold for the similarity score is variable and the fixed number of groups is two.

5. The method according to claim 3, wherein the similarity score is based on a corrected distance value.

6. The method according to claim 1, further comprising:
correcting the group of aligned reads, the correcting includes correcting the sequence data disposed in one or more main positions and the adjacent secondary position region based on one or more nucleotides being disposed in the adjacent secondary position region.

7. The method according to claim 1, wherein each consensus sequence for each group of reads is generated in parallel.

8. A method of processing sequence data to generate a consensus sequence, comprising:
receiving one or more groups of aligned sequence data, the aligned sequence data including one or more aligned reads of sequence data, each read including sequence data disposed at a plurality of main positions and four or more secondary position regions including a plurality of secondary positions disposed adjacent to each of the main positions, wherein each main position comprises one or more nucleotides, wherein the plurality of main positions comprises at least 100 main positions;
correcting the sequence data disposed at one or more main positions in each read based on the sequence data disposed in each adjacent secondary position region;
determining a group of reads with a main position without diversity based on a diversity confidence score for each group of the corrected aligned sequence data, the diversity confidence score being based on a frequency of each nucleotide disposed at each main position in the group and further wherein the group of reads comprises at least 39 reads;
determining legitimate sequence data based on each secondary position region of the group of reads with each main position without diversity in which one or more nucleotides are disposed; and generating a consensus sequence incorporating sequence data disposed at main positions without diversity and the legitimate sequence data disposed at each secondary position region for each group of reads with each main position without diversity, wherein a main position without diversity comprises a main position determined to include only a consensus nucleotide or non-consensus nucleotides with diversity confidence scores outside of a threshold requirement.

9. The method according to claim 8, further comprising:

determining a group of reads with each main position with diversity based on the diversity status of each main position of the group of aligned reads; and classifying the reads of the group of reads with each main position with diversity into a fixed number of groups based on a similarity score.

10. The method according to claim 9, wherein the similarity score represents a proportional relationship between each pair of reads of the group of reads with each main position with diversity based on a number of differences between each main position of the pair.

11. The method according to claim 9, wherein a threshold for the similarity score is variable and the fixed number of groups is two.

12. The method according to claim 10, wherein the similarity score is based on a corrected distance value.

13. The method according to claim 8, further comprising: outputting the consensus sequence.

14. A system for processing sequence data to generate a consensus sequence, comprising:

a memory; and a processor, wherein the processor is configured to cause:

determining a group of reads with a main position without diversity from a group of aligned reads based on diversity status of each main position of the group of aligned reads, the group of aligned reads including sequence data disposed at a plurality of main positions and four or more secondary position regions disposed adjacent to each of the main positions, the diversity status being based on a frequency of one or more nucleotides and/or diversity confidence score of one or more non-consensus nucleotides disposed at each main position in each group, wherein each main position comprises one or more nucleotides, and further wherein a main position without diversity comprises a main position determined to include only a consensus nucleotide or non-consensus nucleotides with diversity confidence scores outside of a threshold requirement, wherein the plurality of main positions comprises at least 100 main positions and further wherein the group of reads comprises at least 39 reads;

determining legitimate sequence data from each secondary position region having one or more nucleotides for each group of reads without diversity; and generating a consensus sequence including sequence data disposed at each main position without diversity and legitimate sequence data disposed at each secondary position region for each group of reads with each main position without diversity.

15. The system according to claim 14, wherein the processor is further configured to cause:

determining a group of reads with each main position with diversity based on the diversity status of each main position of the group of aligned reads; and classifying the reads of the group of reads with each main position with diversity into a fixed number of groups based on a similarity score.

16. The system according to claim 15, wherein the similarity score represents a proportional relationship between each pair of reads of the group of reads with each main position with diversity based on a number of differences between each main position of the pair.

17. The system according to claim 16, wherein a threshold for the similarity score is variable and the fixed number of groups is two.

18. The system according to claim 16, wherein the similarity score is based on a corrected distance value.

19. The system according to claim 14, wherein the processor is further configured to cause:

correcting the group of aligned reads, the correcting includes correcting the sequence data disposed in one or more main positions and the adjacent secondary position region based on one or more nucleotides being disposed in the adjacent secondary position region.

20. The system according to claim 14, wherein the processor is further configured to cause:

outputting the consensus sequence.

* * * * *

```
                            SEQUENCE LISTING

<160> NUMBER OF SEQ ID NOS: 86

<210> SEQ ID NO 1
<211> LENGTH: 39
<212> TYPE: DNA
<213> ORGANISM: Artificial
<220> FEATURE:
<223> OTHER INFORMATION: Computer construct

<400> SEQUENCE: 1
acttaggcac cttacatgaa tggccgtaga gcttttag                           39

<210> SEQ ID NO 2
<211> LENGTH: 47
<212> TYPE: DNA
<213> ORGANISM: Artificial
<220> FEATURE:
<223> OTHER INFORMATION: Computer construct

<400> SEQUENCE: 2
cagcagggaa ccaatacaat gatggacacc taaaagaagc tttttttg                47

<210> SEQ ID NO 3
<211> LENGTH: 46
<212> TYPE: DNA
<213> ORGANISM: Artificial
<220> FEATURE:
<223> OTHER INFORMATION: Computer construct

<400> SEQUENCE: 3
acatttgagg gaaccattac aatgaatgga cacgtagagc ttttag                  46

<210> SEQ ID NO 4
<211> LENGTH: 42
<212> TYPE: DNA
<213> ORGANISM: Artificial
<220> FEATURE:
<223> OTHER INFORMATION: Computer construct

<400> SEQUENCE: 4
acagagggaa ccaatacaat gaatggacac tagagctttt ag                      42

<210> SEQ ID NO 5
<211> LENGTH: 43
<212> TYPE: DNA
<213> ORGANISM: Artificial
<220> FEATURE:
<223> OTHER INFORMATION: Computer construct
```

<400> SEQUENCE: 5
acagaaggga accataacaa gtgaatggac actagagctt tta                43

<210> SEQ ID NO 6
<211> LENGTH: 44
<212> TYPE: DNA
<213> ORGANISM: Artificial
<220> FEATURE:
<223> OTHER INFORMATION: Computer construct

<400> SEQUENCE: 6 cagaggggggg aaccatacaa tgaatggaca ctaagagctt ttag               44

<210> SEQ ID NO 7
<211> LENGTH: 44
<212> TYPE: DNA
<213> ORGANISM: Artificial
<220> FEATURE:
<223> OTHER INFORMATION: Computer construct

<400> SEQUENCE: 7
acagagggaa ccatacaatg aaatggaaac actagagctt ttag               44

<210> SEQ ID NO 8
<211> LENGTH: 45
<212> TYPE: DNA
<213> ORGANISM: Artificial
<220> FEATURE:
<223> OTHER INFORMATION: Computer construct

<400> SEQUENCE: 8
acaggaggga accatacaat gaatggacac tagaggggct tttag              45

<210> SEQ ID NO 9
<211> LENGTH: 48
<212> TYPE: DNA
<213> ORGANISM: Artificial
<220> FEATURE:
<223> OTHER INFORMATION: Computer construct

<400> SEQUENCE: 9
acaggaggaa cccccccacta taacatgaat ggacactaga gcttttta          48

<210> SEQ ID NO 10
<211> LENGTH: 50
<212> TYPE: DNA
<213> ORGANISM: Artificial
<220> FEATURE:
<223> OTHER INFORMATION: Computer construct

<400> SEQUENCE: 10
acagatggaa actcgaggag cacaatgatg gaccactaga gcttttatag         50

<210> SEQ ID NO 11
<211> LENGTH: 41
<212> TYPE: DNA
<213> ORGANISM: Artificial
<220> FEATURE:
<223> OTHER INFORMATION: Computer construct

<400> SEQUENCE: 11
acaagggaac catacaatga atggacacct agagctttta g                  41

<210> SEQ ID NO 12
<211> LENGTH: 42

<212> TYPE: DNA
<213> ORGANISM: Artificial
<220> FEATURE:
<223> OTHER INFORMATION: Computer construct

<400> SEQUENCE: 12
acagatggaa cataacaatg aatggacaac tagagctttt ag        42

<210> SEQ ID NO 13
<211> LENGTH: 45
<212> TYPE: DNA
<213> ORGANISM: Artificial
<220> FEATURE:
<223> OTHER INFORMATION: Computer construct

<400> SEQUENCE: 13
acagagggaa cccatacaat gaatggacgc cactagagct tttag        45

<210> SEQ ID NO 14
<211> LENGTH: 42
<212> TYPE: DNA
<213> ORGANISM: Artificial
<220> FEATURE:
<223> OTHER INFORMATION: Computer construct

<400> SEQUENCE: 14
acagagggaa ccatacaatt gaatggacac tagagctttt ag        42

<210> SEQ ID NO 15
<211> LENGTH: 40
<212> TYPE: DNA
<213> ORGANISM: Artificial
<220> FEATURE:
<223> OTHER INFORMATION: Computer construct

<400> SEQUENCE: 15
acagagggaa ccatacaatg aatcggacac tagactttag        40

<210> SEQ ID NO 16
<211> LENGTH: 46
<212> TYPE: DNA
<213> ORGANISM: Artificial
<220> FEATURE:
<223> OTHER INFORMATION: Computer construct

<400> SEQUENCE: 16
acagaggtaa ccaatacaaa tgaatggaac actagagctt tttata        46

<210> SEQ ID NO 17
<211> LENGTH: 40
<212> TYPE: DNA
<213> ORGANISM: Artificial
<220> FEATURE:
<223> OTHER INFORMATION: Computer construct

<400> SEQUENCE: 17
acagagggaa ccatacaata atggaccact aggcttttag        40

<210> SEQ ID NO 18
<211> LENGTH: 41
<212> TYPE: DNA
<213> ORGANISM: Artificial
<220> FEATURE:
<223> OTHER INFORMATION: Computer construct

<400> SEQUENCE: 18
acagagggaa ccatacaatg atggacacta gagctttta g                        41

<210> SEQ ID NO 19
<211> LENGTH: 43
<212> TYPE: DNA
<213> ORGANISM: Artificial
<220> FEATURE:
<223> OTHER INFORMATION: Computer construct

<400> SEQUENCE: 19
acagagggaa ccatacaatg aatggcacac tagagctttt tag                     43

<210> SEQ ID NO 20
<211> LENGTH: 43
<212> TYPE: DNA
<213> ORGANISM: Artificial
<220> FEATURE:
<223> OTHER INFORMATION: Computer construct

<400> SEQUENCE: 20
acagaggtga accattacaa tcgaattgac acagagcttt tag                     43

<210> SEQ ID NO 21
<211> LENGTH: 40
<212> TYPE: DNA
<213> ORGANISM: Artificial
<220> FEATURE:
<223> OTHER INFORMATION: Computer construct

<400> SEQUENCE: 21
accaggaggg aacgcataca tgaatggaca cgggttttag                         40

<210> SEQ ID NO 22
<211> LENGTH: 42
<212> TYPE: DNA
<213> ORGANISM: Artificial
<220> FEATURE:
<223> OTHER INFORMATION: Computer construct

<400> SEQUENCE: 22
acagacggga accatacaat gaatggacac tagagctttt ag                      42

<210> SEQ ID NO 23
<211> LENGTH: 47
<212> TYPE: DNA
<213> ORGANISM: Artificial
<220> FEATURE:
<223> OTHER INFORMATION: Computer construct

<400> SEQUENCE: 23
acaagaggga accataaaac aatgaaatga gacatagacg cttttag                 47

<210> SEQ ID NO 24
<211> LENGTH: 42
<212> TYPE: DNA
<213> ORGANISM: Artificial
<220> FEATURE:
<223> OTHER INFORMATION: Computer construct

<400> SEQUENCE: 24
acagaggaac cataccatga atggaacact agagcttttt ag                      42

<210> SEQ ID NO 25
<211> LENGTH: 44
<212> TYPE: DNA
<213> ORGANISM: Artificial

```
<220> FEATURE:
<223> OTHER INFORMATION: Computer construct

<400> SEQUENCE: 25
acagacggaa cgcagtacaa tgaatgcaca ctaggagctt ttag          44

<210> SEQ ID NO 26
<211> LENGTH: 44
<212> TYPE: DNA
<213> ORGANISM: Artificial
<220> FEATURE:
<223> OTHER INFORMATION: Computer construct

<400> SEQUENCE: 26
acagagggag cgcatacaac tgaatgggag cctagagctt ttag          44

<210> SEQ ID NO 27
<211> LENGTH: 52
<212> TYPE: DNA
<213> ORGANISM: Artificial
<220> FEATURE:
<223> OTHER INFORMATION: Computer construct

<400> SEQUENCE: 27
acacggaggg aacggcatac tattatggta tgtgtgtcga ctagagcttt ag    52

<210> SEQ ID NO 28
<211> LENGTH: 38
<212> TYPE: DNA
<213> ORGANISM: Artificial
<220> FEATURE:
<223> OTHER INFORMATION: Computer construct

<400> SEQUENCE: 28
acagaggaac cattacaaga aagacacaag agcttaag          38

<210> SEQ ID NO 29
<211> LENGTH: 42
<212> TYPE: DNA
<213> ORGANISM: Artificial
<220> FEATURE:
<223> OTHER INFORMATION: Computer construct

<400> SEQUENCE: 29
acagagggaa ccatacaatg aatggacact aagactttta ag          42

<210> SEQ ID NO 30
<211> LENGTH: 40
<212> TYPE: DNA
<213> ORGANISM: Artificial
<220> FEATURE:
<223> OTHER INFORMATION: Computer construct

<400> SEQUENCE: 30
acagagggaa catacaatga atggacctta aggcttttag          40

<210> SEQ ID NO 31
<211> LENGTH: 47
<212> TYPE: DNA
<213> ORGANISM: Artificial
<220> FEATURE:
<223> OTHER INFORMATION: Computer construct

<400> SEQUENCE: 31
acagcgggaa ccataccaag tgaatttgga gcactagagc ttttaag          47
```

```
<210> SEQ ID NO 32
<211> LENGTH: 41
<212> TYPE: DNA
<213> ORGANISM: Artificial
<220> FEATURE:
<223> OTHER INFORMATION: Computer construct

<400> SEQUENCE: 32
cagagggaac catacaatga atggaccacc tagacttta g                  41

<210> SEQ ID NO 33
<211> LENGTH: 42
<212> TYPE: DNA
<213> ORGANISM: Artificial
<220> FEATURE:
<223> OTHER INFORMATION: Computer construct

<400> SEQUENCE: 33
acagagggaa cccatacaag aatggacatt agagcttttt ag                42

<210> SEQ ID NO 34
<211> LENGTH: 46
<212> TYPE: DNA
<213> ORGANISM: Artificial
<220> FEATURE:
<223> OTHER INFORMATION: Computer construct

<400> SEQUENCE: 34
acagagggaa ccattacaag aaagttggac acgaagcttt tgtgag            46

<210> SEQ ID NO 35
<211> LENGTH: 40
<212> TYPE: DNA
<213> ORGANISM: Artificial
<220> FEATURE:
<223> OTHER INFORMATION: Computer construct

<400> SEQUENCE: 35
acaaggaagc catacaatga atggacatag agcttttag                    40

<210> SEQ ID NO 36
<211> LENGTH: 45
<212> TYPE: DNA
<213> ORGANISM: Artificial
<220> FEATURE:
<223> OTHER INFORMATION: Computer construct

<400> SEQUENCE: 36
acaggaaggg aaaccataca atgaatggga aactagagct tttag             45

<210> SEQ ID NO 37
<211> LENGTH: 49
<212> TYPE: DNA
<213> ORGANISM: Artificial
<220> FEATURE:
<223> OTHER INFORMATION: Computer construct

<400> SEQUENCE: 37
acaagcccag gggaaaccat acaatgaagg gaacactaga gcttttag          49

<210> SEQ ID NO 38
<211> LENGTH: 42
<212> TYPE: DNA
<213> ORGANISM: Artificial
<220> FEATURE:
<223> OTHER INFORMATION: Computer construct
```

```
<400> SEQUENCE: 38
acagagggaa ccatacattg aatggacatc tagatgcttt ag                    42

<210> SEQ ID NO 39
<211> LENGTH: 41
<212> TYPE: DNA
<213> ORGANISM: Artificial
<220> FEATURE:
<223> OTHER INFORMATION: Computer construct

<400> SEQUENCE: 39
acagagggag accatacaat gaatggacac tgagctttta g                     41

<210> SEQ ID NO 40
<211> LENGTH: 6
<212> TYPE: DNA
<213> ORGANISM: Artificial
<220> FEATURE:
<223> OTHER INFORMATION: Computer construct

<400> SEQUENCE: 40 acttag                                                             6

<210> SEQ ID NO 41
<211> LENGTH: 6
<212> TYPE: DNA
<213> ORGANISM: Artificial
<220> FEATURE:
<223> OTHER INFORMATION: Computer construct

<400> SEQUENCE: 41 cagcag                                                             6

<210> SEQ ID NO 42
<211> LENGTH: 9
<212> TYPE: DNA
<213> ORGANISM: Artificial
<220> FEATURE:
<223> OTHER INFORMATION: Computer construct

<400> SEQUENCE: 42 acatttgag                                                          9

<210> SEQ ID NO 43
<211> LENGTH: 6
<212> TYPE: DNA
<213> ORGANISM: Artificial
<220> FEATURE:
<223> OTHER INFORMATION: Computer construct

<400> SEQUENCE: 43 acagag                                                             6

<210> SEQ ID NO 44
<211> LENGTH: 6
<212> TYPE: DNA
<213> ORGANISM: Artificial
<220> FEATURE:
<223> OTHER INFORMATION: Computer construct

<400> SEQUENCE: 44 acttag                                                             6

<210> SEQ ID NO 45
```

```
<211> LENGTH: 3
<212> TYPE: DNA
<213> ORGANISM: Artificial
<220> FEATURE:
<223> OTHER INFORMATION: Computer construct

<400> SEQUENCE: 45 cag                                                                      3

<210> SEQ ID NO 46
<211> LENGTH: 4
<212> TYPE: DNA
<213> ORGANISM: Artificial
<220> FEATURE:
<223> OTHER INFORMATION: Computer construct

<400> SEQUENCE: 46 acag                                                                     4

<210> SEQ ID NO 47
<211> LENGTH: 6
<212> TYPE: DNA
<213> ORGANISM: Artificial
<220> FEATURE:
<223> OTHER INFORMATION: Computer construct

<400> SEQUENCE: 47 acagag                                                                   6

<210> SEQ ID NO 48
<211> LENGTH: 33
<212> TYPE: DNA
<213> ORGANISM: Artificial
<220> FEATURE:
<223> OTHER INFORMATION: Computer construct

<400> SEQUENCE: 48
acttaggcac cttacatgaa tggcagagct ttg                                    33

<210> SEQ ID NO 49
<211> LENGTH: 27
<212> TYPE: DNA
<213> ORGANISM: Artificial
<220> FEATURE:
<223> OTHER INFORMATION: Computer construct

<400> SEQUENCE: 49
cagggaacta caatgatgga cgttttg                                           27

<210> SEQ ID NO 50
<211> LENGTH: 35
<212> TYPE: DNA
<213> ORGANISM: Artificial
<220> FEATURE:
<223> OTHER INFORMATION: Computer construct

<400> SEQUENCE: 50
acagggaacc acaatgaatg gacaagagct tttag                                  35

<210> SEQ ID NO 51
<211> LENGTH: 39
<212> TYPE: DNA
<213> ORGANISM: Artificial
<220> FEATURE:
<223> OTHER INFORMATION: Computer construct

<400> SEQUENCE: 51
```
acagagggaa ctacaatgaa tggacactag agcttttag          39

<210> SEQ ID NO 52
<211> LENGTH: 34
<212> TYPE: DNA
<213> ORGANISM: Artificial
<220> FEATURE:
<223> OTHER INFORMATION: Computer construct

<400> SEQUENCE: 52
acagggaacc acagaatgga cactagagct ttta               34

<210> SEQ ID NO 53
<211> LENGTH: 36
<212> TYPE: DNA
<213> ORGANISM: Artificial
<220> FEATURE:
<223> OTHER INFORMATION: Computer construct

<400> SEQUENCE: 53
cagggaacca tacaatgaat ggacacgagc ttttag             36

<210> SEQ ID NO 54
<211> LENGTH: 37
<212> TYPE: DNA
<213> ORGANISM: Artificial
<220> FEATURE:
<223> OTHER INFORMATION: Computer construct

<400> SEQUENCE: 54
acagagggaa ccatacaata tgcactagag cttttag            37

<210> SEQ ID NO 55
<211> LENGTH: 37
<212> TYPE: DNA
<213> ORGANISM: Artificial
<220> FEATURE:
<223> OTHER INFORMATION: Computer construct

<400> SEQUENCE: 55
acagggaacc atacaatgaa tggacactag attttag            37

<210> SEQ ID NO 56
<211> LENGTH: 30
<212> TYPE: DNA
<213> ORGANISM: Artificial
<220> FEATURE:
<223> OTHER INFORMATION: Computer construct

<400> SEQUENCE: 56
acaggaacaa tgaatggaca ctagagcttt                    30

<210> SEQ ID NO 57
<211> LENGTH: 28
<212> TYPE: DNA
<213> ORGANISM: Artificial
<220> FEATURE:
<223> OTHER INFORMATION: Computer construct

<400> SEQUENCE: 57
acaggaaaac aatgatggac tagagtag                      28

<210> SEQ ID NO 58
<211> LENGTH: 38
<212> TYPE: DNA

<213> ORGANISM: Artificial
<220> FEATURE:
<223> OTHER INFORMATION: Computer construct

<400> SEQUENCE: 58
acaagggaac catacaatga atggactaga gcttttag         38

<210> SEQ ID NO 59
<211> LENGTH: 36
<212> TYPE: DNA
<213> ORGANISM: Artificial
<220> FEATURE:
<223> OTHER INFORMATION: Computer construct

<400> SEQUENCE: 59
acagatggaa cacaatgaat ggactagagc ttttag           36

<210> SEQ ID NO 60
<211> LENGTH: 37
<212> TYPE: DNA
<213> ORGANISM: Artificial
<220> FEATURE:
<223> OTHER INFORMATION: Computer construct

<400> SEQUENCE: 60
acagagggac atacaatgaa tggactagag cttttag          37

<210> SEQ ID NO 61
<211> LENGTH: 39
<212> TYPE: DNA
<213> ORGANISM: Artificial
<220> FEATURE:
<223> OTHER INFORMATION: Computer construct

<400> SEQUENCE: 61
acagagggaa ccatacaaaa tggacactag agcttttag        39

<210> SEQ ID NO 62
<211> LENGTH: 37
<212> TYPE: DNA
<213> ORGANISM: Artificial
<220> FEATURE:
<223> OTHER INFORMATION: Computer construct

<400> SEQUENCE: 62
acagagggaa ccatacaatg aagacactag actttag          37

<210> SEQ ID NO 63
<211> LENGTH: 30
<212> TYPE: DNA
<213> ORGANISM: Artificial
<220> FEATURE:
<223> OTHER INFORMATION: Computer construct

<400> SEQUENCE: 63
cagaggtaac taatgaatgc actagagttt                  30

<210> SEQ ID NO 64
<211> LENGTH: 37
<212> TYPE: DNA
<213> ORGANISM: Artificial
<220> FEATURE:
<223> OTHER INFORMATION: Computer construct

<400> SEQUENCE: 64
acagagggaa ccatacaata atggactagg cttttag          37

<210> SEQ ID NO 65
<211> LENGTH: 38
<212> TYPE: DNA
<213> ORGANISM: Artificial
<220> FEATURE:
<223> OTHER INFORMATION: Computer construct

<400> SEQUENCE: 65
acagagggaa ccatacaatg atggacacta gagtttag                           38

<210> SEQ ID NO 66
<211> LENGTH: 37
<212> TYPE: DNA
<213> ORGANISM: Artificial
<220> FEATURE:
<223> OTHER INFORMATION: Computer construct

<400> SEQUENCE: 66
acagagggaa ccatacaatg aatgcactag agctttg                            37

<210> SEQ ID NO 67
<211> LENGTH: 34
<212> TYPE: DNA
<213> ORGANISM: Artificial
<220> FEATURE:
<223> OTHER INFORMATION: Computer construct

<400> SEQUENCE: 67
acagagaacc acaaaattga cacagagctt ttag                               34

<210> SEQ ID NO 68
<211> LENGTH: 31
<212> TYPE: DNA
<213> ORGANISM: Artificial
<220> FEATURE:
<223> OTHER INFORMATION: Computer construct

<400> SEQUENCE: 68
agggaaatac atgaatggac acgggtttta g                                  31

<210> SEQ ID NO 69
<211> LENGTH: 39
<212> TYPE: DNA
<213> ORGANISM: Artificial
<220> FEATURE:
<223> OTHER INFORMATION: Computer construct

<400> SEQUENCE: 69
acagggaacc atacaatgaa tggacactag agcttttag                          39

<210> SEQ ID NO 70
<211> LENGTH: 30
<212> TYPE: DNA
<213> ORGANISM: Artificial
<220> FEATURE:
<223> OTHER INFORMATION: Computer construct

<400> SEQUENCE: 70
agagggaacc acaatataca tagcttttag                                    30

<210> SEQ ID NO 71
<211> LENGTH: 36
<212> TYPE: DNA
<213> ORGANISM: Artificial
<220> FEATURE:

<223> OTHER INFORMATION: Computer construct

<400> SEQUENCE: 71
acagaggaac cataccatga atgcactaga gtttag 36

<210> SEQ ID NO 72
<211> LENGTH: 35
<212> TYPE: DNA
<213> ORGANISM: Artificial
<220> FEATURE:
<223> OTHER INFORMATION: Computer construct

<400> SEQUENCE: 72
acagacggaa acaatgaatg cacactagct tttag 35

<210> SEQ ID NO 73
<211> LENGTH: 32
<212> TYPE: DNA
<213> ORGANISM: Artificial
<220> FEATURE:
<223> OTHER INFORMATION: Computer construct

<400> SEQUENCE: 73
acagagggag atacagaagc tagagctttt ag 32

<210> SEQ ID NO 74
<211> LENGTH: 24
<212> TYPE: DNA
<213> ORGANISM: Artificial
<220> FEATURE:
<223> OTHER INFORMATION: Computer construct

<400> SEQUENCE: 74
acgggaaata tgtctagagc ttta 24

<210> SEQ ID NO 75
<211> LENGTH: 35
<212> TYPE: DNA
<213> ORGANISM: Artificial
<220> FEATURE:
<223> OTHER INFORMATION: Computer construct

<400> SEQUENCE: 75
acagaggaac cacaagaaag acacaagagc ttaag 35

<210> SEQ ID NO 76
<211> LENGTH: 36
<212> TYPE: DNA
<213> ORGANISM: Artificial
<220> FEATURE:
<223> OTHER INFORMATION: Computer construct

<400> SEQUENCE: 76
acagagggaa ccatacaatg aatggacact aatttt 36

<210> SEQ ID NO 77
<211> LENGTH: 34
<212> TYPE: DNA
<213> ORGANISM: Artificial
<220> FEATURE:
<223> OTHER INFORMATION: Computer construct

<400> SEQUENCE: 77
acagagggaa catacaatga atggaccatt ttag 34

```
<210> SEQ ID NO 78
<211> LENGTH: 31
<212> TYPE: DNA
<213> ORGANISM: Artificial
<220> FEATURE:
<223> OTHER INFORMATION: Computer construct

<400> SEQUENCE: 78
acagcgggaa ccatagagga ctagagcttt g                              31

<210> SEQ ID NO 79
<211> LENGTH: 35
<212> TYPE: DNA
<213> ORGANISM: Artificial
<220> FEATURE:
<223> OTHER INFORMATION: Computer construct

<400> SEQUENCE: 79
cagagggaac catacaatga atggtagact tttag                          35

<210> SEQ ID NO 80
<211> LENGTH: 36
<212> TYPE: DNA
<213> ORGANISM: Artificial
<220> FEATURE:
<223> OTHER INFORMATION: Computer construct

<400> SEQUENCE: 80
acagagggaa ctacaagaat ggacattaga gctttg                         36

<210> SEQ ID NO 81
<211> LENGTH: 28
<212> TYPE: DNA
<213> ORGANISM: Artificial
<220> FEATURE:
<223> OTHER INFORMATION: Computer construct

<400> SEQUENCE: 81
acagagggaa ccacaaggac acgaagtg                                  28

<210> SEQ ID NO 82
<211> LENGTH: 33
<212> TYPE: DNA
<213> ORGANISM: Artificial
<220> FEATURE:
<223> OTHER INFORMATION: Computer construct

<400> SEQUENCE: 82
acaaggacat acaatgaatg gacatagagc ttt                            33

<210> SEQ ID NO 83
<211> LENGTH: 34
<212> TYPE: DNA
<213> ORGANISM: Artificial
<220> FEATURE:
<223> OTHER INFORMATION: Computer construct

<400> SEQUENCE: 83
acaggacata caatgaatga actagagctt ttag                           34

<210> SEQ ID NO 84
<211> LENGTH: 30
<212> TYPE: DNA
<213> ORGANISM: Artificial
<220> FEATURE:
<223> OTHER INFORMATION: Computer construct
```

```
<400> SEQUENCE: 84
agaccataca atgaaggcac tagagtttag                                          30

<210> SEQ ID NO 85
<211> LENGTH: 36
<212> TYPE: DNA
<213> ORGANISM: Artificial
<220> FEATURE:
<223> OTHER INFORMATION: Computer construct

<400> SEQUENCE: 85
acagagggaa ccatacattg aatggactag ctttag                                   36

<210> SEQ ID NO 86
<211> LENGTH: 38
<212> TYPE: DNA
<213> ORGANISM: Artificial
<220> FEATURE:
<223> OTHER INFORMATION: Computer construct

<400> SEQUENCE: 86
acagagggcc atacaatgaa tggacactga gcttttag                                 38
```